(12) United States Patent
Lundberg

(10) Patent No.: US 8,425,442 B2
(45) Date of Patent: Apr. 23, 2013

(54) ANKLE STABILIZER

(76) Inventor: Leslie C. Lundberg, Carter Lake, IA (US)

(*) Notice: Subject to any disclaimer, the term of this patent is extended or adjusted under 35 U.S.C. 154(b) by 1016 days.

(21) Appl. No.: 12/414,378

(22) Filed: Mar. 30, 2009

(65) Prior Publication Data
US 2009/0247923 A1    Oct. 1, 2009

Related U.S. Application Data

(60) Provisional application No. 61/072,251, filed on Mar. 28, 2008.

(51) Int. Cl.
| | |
|---|---|
| A41D 19/00 | (2006.01) |
| A61F 5/37 | (2006.01) |
| A61F 13/00 | (2006.01) |
| A61F 5/00 | (2006.01) |
| A61F 13/06 | (2006.01) |
| A61B 19/00 | (2006.01) |

(52) U.S. Cl.
USPC .............. 602/27; 2/161.3; 128/846; 128/869; 128/882; 602/5; 602/23; 602/28; 602/29; 602/30; 602/60; 602/61; 602/62; 602/65

(58) Field of Classification Search .............. 602/5, 23, 602/27–30, 60–62, 65; 128/846, 869, 882; 2/161.3
See application file for complete search history.

(56) References Cited

U.S. PATENT DOCUMENTS

| 540,931 | A | 6/1895 | Walkey |
|---|---|---|---|
| 3,506,000 | A | 4/1970 | Baker |
| 4,280,489 | A | 7/1981 | Johnson, Jr. |
| 4,313,433 | A | 2/1982 | Cramer |
| 4,865,023 | A | 9/1989 | Craythorne et al. |
| 4,926,846 | A | 5/1990 | Nassar |
| RE33,395 | E | 10/1990 | Peters |
| 4,962,768 | A | 10/1990 | Stromgren et al. |
| 4,982,733 | A | 1/1991 | Broadhurst et al. |
| 5,031,607 | A | 7/1991 | Peters |
| 5,067,486 | A | 11/1991 | Hely |
| 5,199,941 | A | 4/1993 | Makinen |
| 5,217,431 | A * | 6/1993 | Toronto et al. .................. 602/27 |
| 5,339,499 | A | 8/1994 | Kennedy et al. |
| 5,366,439 | A | 11/1994 | Peters |
| 5,507,720 | A | 4/1996 | Lampropoulos |
| 5,676,641 | A | 10/1997 | Arensdorf et al. |
| 5,944,678 | A * | 8/1999 | Hubbard ......................... 602/27 |
| 6,053,884 | A | 4/2000 | Peters |
| 6,056,713 | A | 5/2000 | Hayashi |
| 6,126,625 | A | 10/2000 | Lundberg |
| 6,503,218 | B1 | 1/2003 | Ascheman |
| 6,524,266 | B1 | 2/2003 | Peters |
| 6,629,945 | B1 | 10/2003 | Stromgren |
| 6,663,583 | B1 | 12/2003 | Janis |
| 6,749,578 | B2 | 6/2004 | Peters |

(Continued)

*Primary Examiner* — Patricia Bianco
*Assistant Examiner* — Brandon L Jackson
(74) *Attorney, Agent, or Firm* — Hovey Williams LLP

(57) ABSTRACT

An ankle brace is configured to provide lateral and/or medial support of an ankle joint between the leg and foot and broadly includes an upper brace anchor secured to the leg above malleoli of the ankle joint and a lower brace anchor secured below the foot. The anchors are interconnected by a stabilizing strap that is tensioned between the anchors and serves to restrict inversion and/or eversion of the foot. The anchors and strap are also dimensioned and configured to permit dorsiflexion and plantar flexion of the foot.

44 Claims, 11 Drawing Sheets

U.S. PATENT DOCUMENTS 6,858,017 B2  2/2005  Peters
7,267,656 B2  9/2007  Cooper

2006/0084899 A1  4/2006  Verkade et al.

* cited by examiner

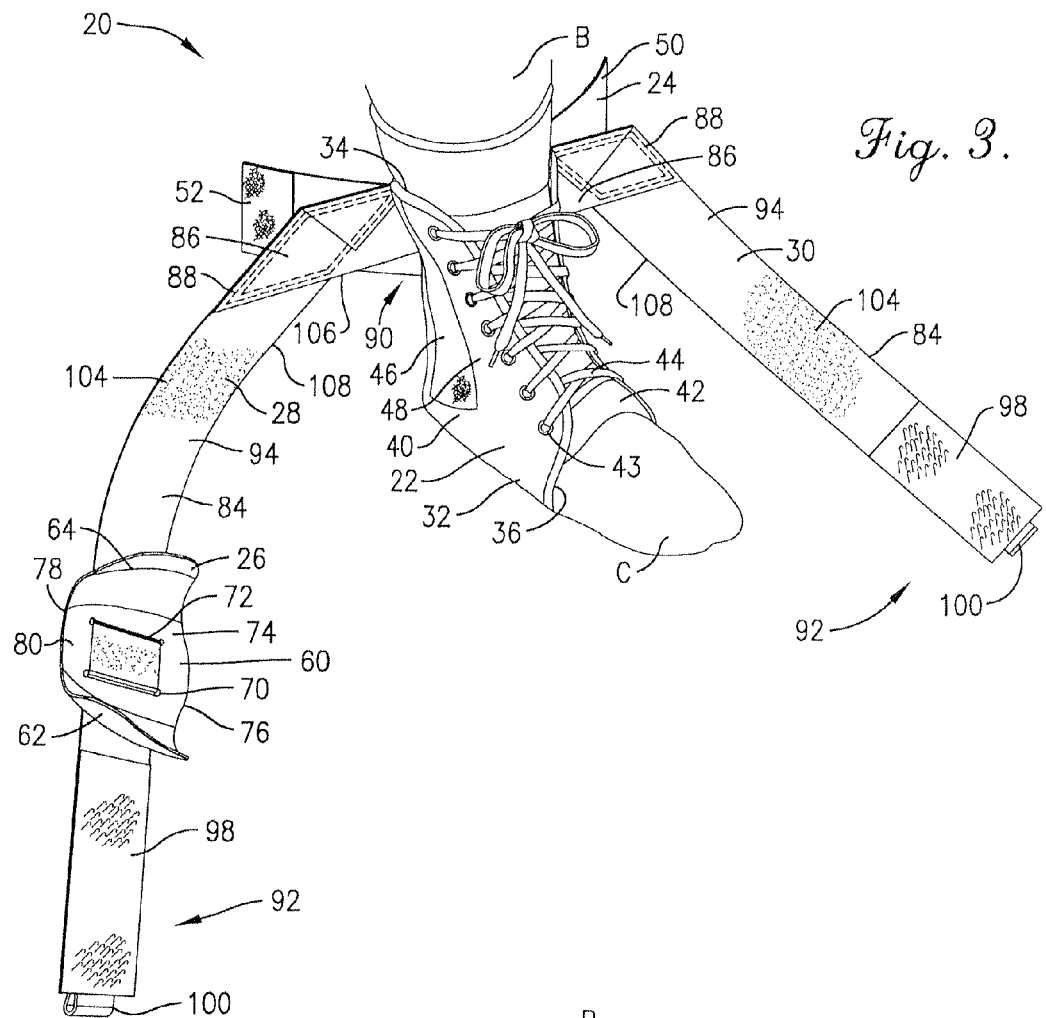
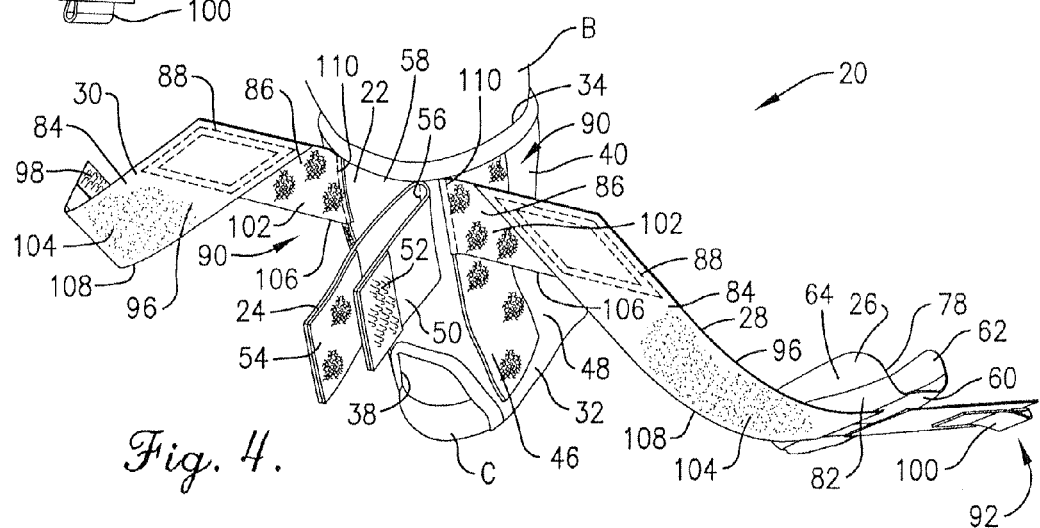

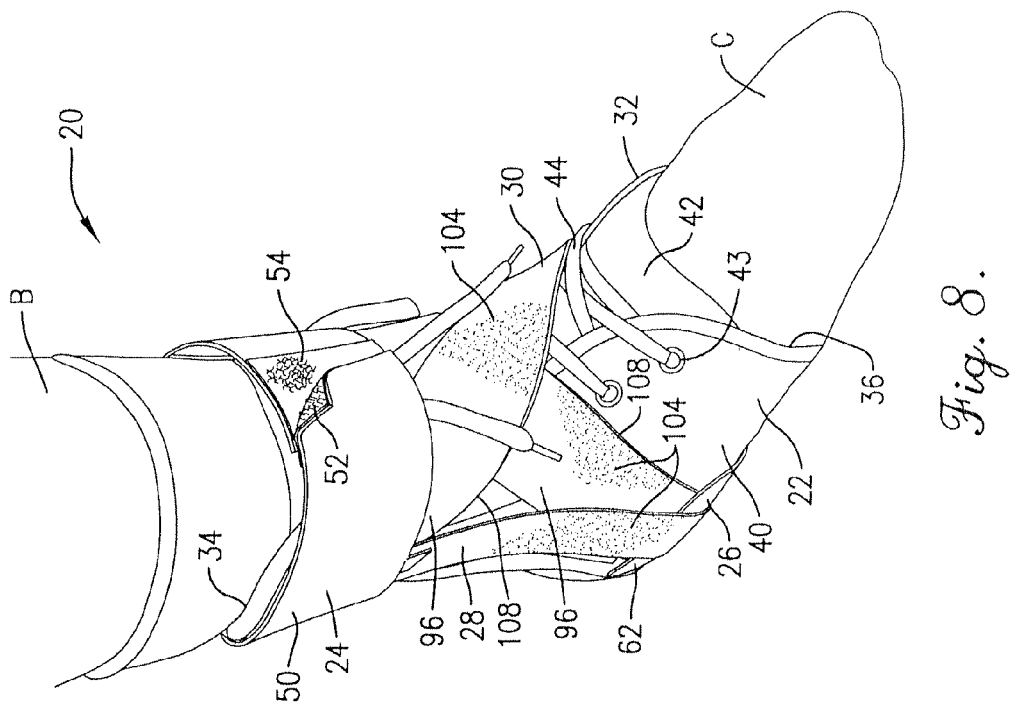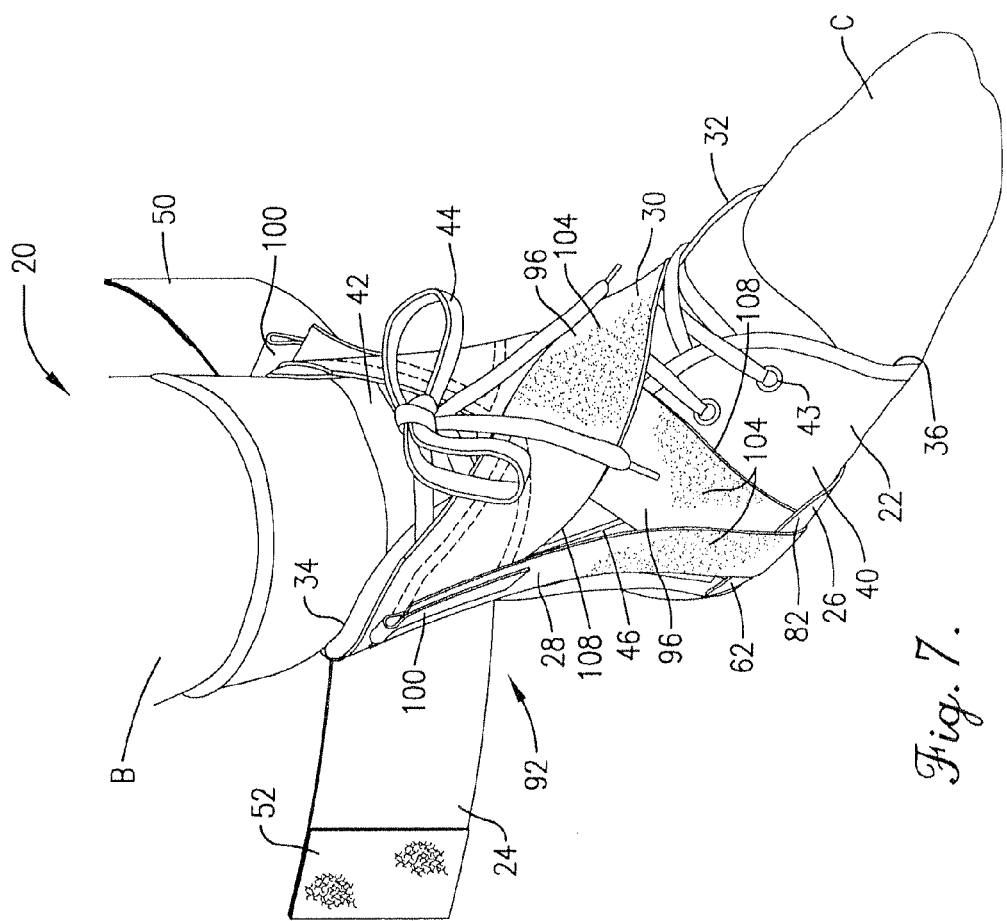

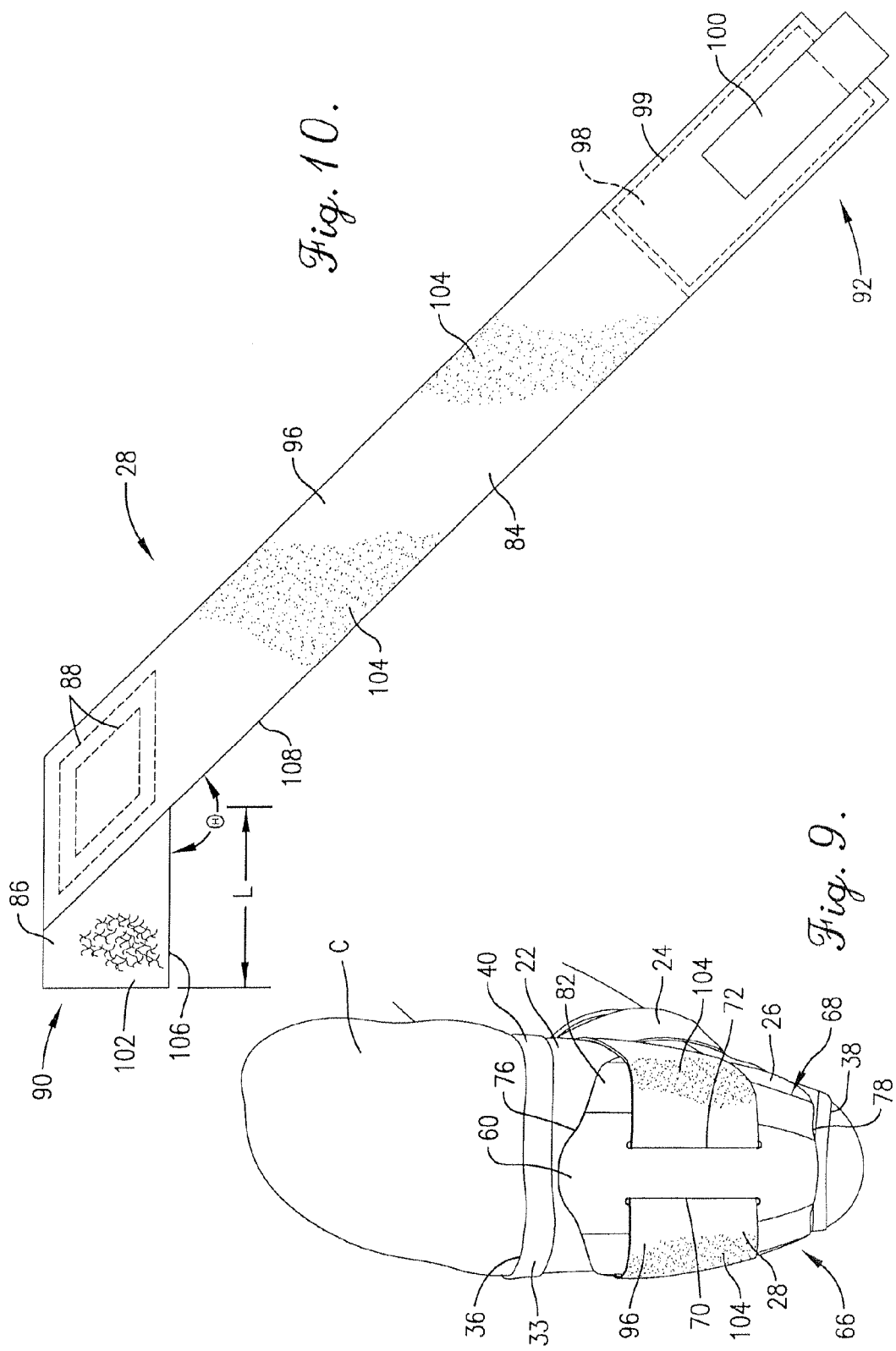

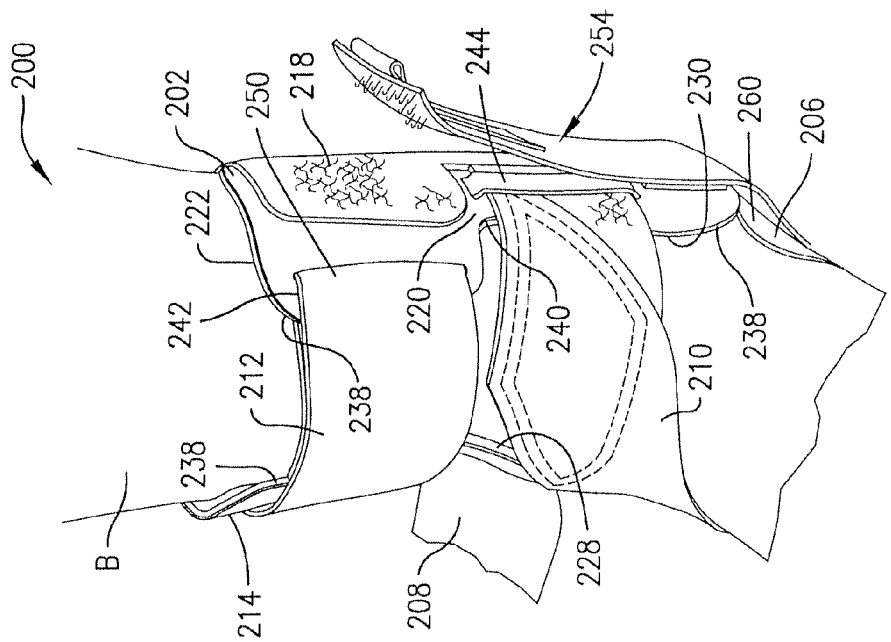
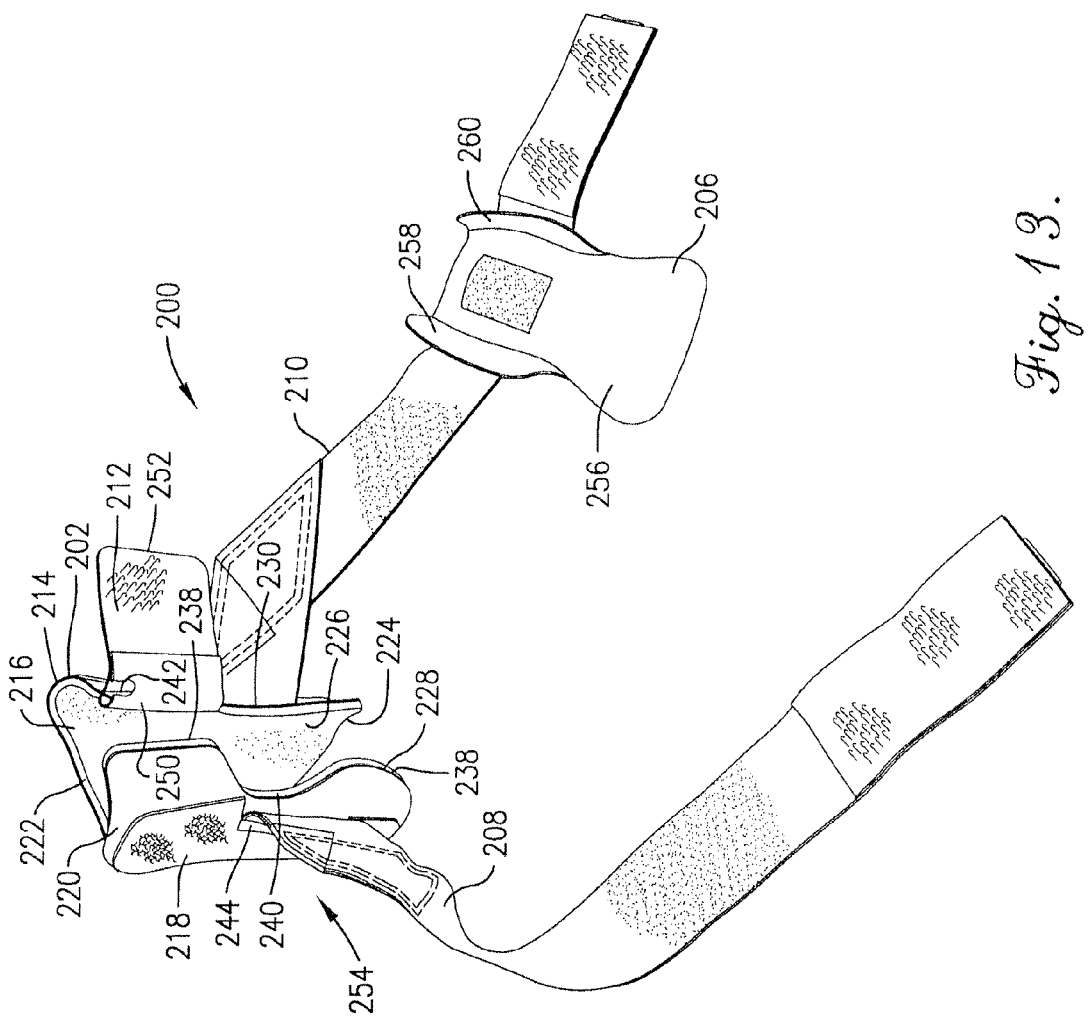

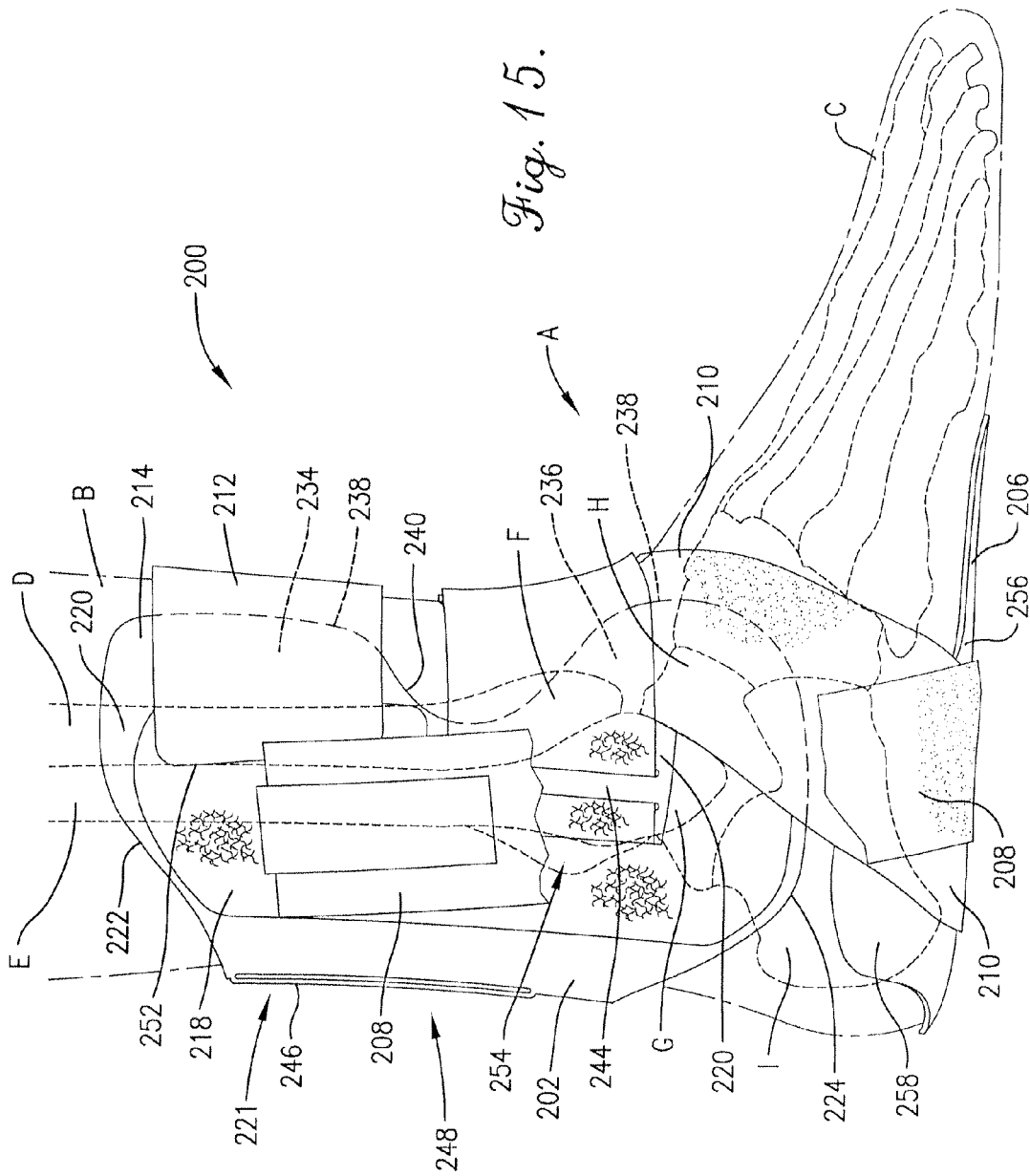

ANKLE STABILIZER

RELATED APPLICATION

This application claims the benefit of U.S. Provisional Application Ser. No. 61/072,251, filed Mar. 28, 2008, entitled ANKLE STABILIZER, which is hereby incorporated in its entirety by reference herein.

BACKGROUND

1. Field

The present invention relates generally to orthotic medical devices. More specifically, embodiments of the present invention concern an ankle stabilizer that supports an ankle joint by restricting inversion and/or eversion of the foot while permitting plantar flexion and/or dorsiflexion of the foot.

2. Discussion of Prior Art

The ankle comprises a synovial joint and connects the foot to the tibia and fibula of the leg. The ankle and foot include numerous bones that are interconnected by ligaments, muscles, and other tissues. These ligaments are prone to various types of high and low ankle sprains caused by excessive foot movement, such as eversion (when the foot is turned outwardly relative to the leg and causes undue stretching of medial ligaments) or inversion (when the foot is turned inwardly relative to the leg and causes undue stretching of lateral ligaments) of the ankle.

Various conventional devices have been employed to support or immobilize the ankle joint and thereby provide orthotic treatment of sprains. For example, a splint-type brace is particularly used for immobilizing the ankle joint during the acute stage of ankle injury. However, this type of brace is typically bulky and therefore cannot be worn inside a shoe or clothing. Another serious problem with a "splint-type" brace is that essentially all joint function is prevented, which restricts activity involving use of the joint and can thereby slow rehabilitation and promote muscle atrophy.

Wrapping of the joint with a cloth bandage or tape is another conventional technique for immobilizing a joint. Although cloth or tape wraps are more comfortable and less bulky than "splint-type" braces, the wraps likewise immobilize the joint and therefore present the same problems of atrophy, lack of performance during the rehabilitation stage of the injury, and excessive restriction of joint function. Cloth and tape wraps are particularly problematic because they encircle the joint and adjacent body parts, such as the top of the foot, and also preclude necessary dorsi and plantar flexion of the ankle joint.

Braces have been designed for use during the rehabilitation stage of injuries. Rehabilitative braces typically include a pliable sleeve formed of elastic material for placement on the joint and adjacent body parts. For example, a rehabilitative ankle brace traditionally comprises a boot-shaped sleeve that is tightened about the lower leg, ankle joint and foot by suitable lacing. Although this type of brace is comfortable and capable of being worn within a shoe, the sleeve itself provides little support to the joint. Accordingly, the sleeve would not be effective during the acute stage of an injury because of its failure to sufficiently restrict movement of the joint. Even when the sleeve is used for rehabilitative purposes, it restricts movement of the joint in virtually any direction and, consequently, fails to permit dorsiflexion and plantar flexion of the foot. It will be appreciated that rehabilitative sleeves are also often used as a prophylaxis for reducing the risk of re-injury.

Rehabilitative sleeves have been provided with various structure in an attempt to broaden their application to include treatment during the acute stage of the injury. For example, sleeves have been provided with rigid splints inserted into pockets formed along the sleeve. However, this type of brace still presents the same problems noted above.

Accordingly, there is a need in the art for improved orthotic devices that treat ankle sprains or serve as a prophylaxis by restricting lateral and medial movement of the foot while permitting dorsiflexion and plantar flexion.

SUMMARY

Embodiments of the present invention provide an ankle stabilizer that does not suffer from the problems and limitations of the prior art ankle wraps, sleeves, and braces set forth above.

A first aspect of the present invention concerns an ankle brace configured to provide support of the ankle joint between the leg and foot. The ankle brace broadly includes an upper brace structure, a heel plate, and an elongated strap. The upper brace structure is configured to be attached to the leg and anchor the ankle brace above malleoli of the joint. The heel plate is positioned below the upper brace structure and is configured to be located below the heel to anchor the ankle brace below the malleoli. The heel plate includes a substantially flat base and upright lateral and medial walls that extend upwardly from the base. The elongated strap is adjustably attached to the upper brace structure and heel plate and extends exteriorly along at least one of the lateral and medial walls. The heel plate presents an open longitudinal channel extending between the lateral and medial walls and operable to receive the foot. The heel plate has anterior and posterior open channel ends so that the channel is devoid of an upright wall, with adjustable tensioning of the strap serving to flex the at least one of the lateral and medial walls relative to the base to conform the heel plate to the heel.

A second aspect of the present invention concerns an ankle brace configured to provide support of the ankle joint between the leg and foot. The ankle brace broadly includes an upper brace structure and an elongated strap. The upper brace structure is configured to be attached to the leg and anchor the ankle brace above malleoli of the joint. The elongated strap includes first and second strap sections. The upper brace structure presents lateral and medial sides configured to engage the strap. The first strap section is attached to the upper brace structure at an attachment location, with the first strap section extending horizontally from the attachment location. The second strap section is joined to the first strap section at a downward angle spaced from the attachment location so that the second strap section is configured and dimensioned to extend between the lateral and medial sides to permit substantially unrestricted dorsiflexion of the foot.

A third aspect of the present invention concerns an ankle brace configured to provide support of the ankle joint between the leg and foot. The ankle brace broadly includes an upper brace structure, a generally horizontal adjustably tensionable closure strip, and an elongated strap. The upper brace structure is configured to be attached to the leg and anchor the ankle brace above malleoli of the joint. The upper brace structure includes an arcuate unitary hard shell that presents proximal and distal open ends, a closed posterior portion extending between the ends, and lateral and medial sides projecting from the posterior portion and extending between the proximal and distal open ends. The hard shell presents an adjustable leg-receiving slot that extends between the open ends. The hard shell extends continuously between the open ends to cover the malleoli and present integral proximal and distal shell segments, with the proximal shell segment dimensioned and configured to be attached above the malleoli and the distal shell segment dimensioned and configured to extend below the malleoli. The generally horizontal adjustably tensionable closure strip is attached to sides of the proximal shell segment to selectively close the slot and constrict the proximal shell segment about the leg. The elongated strap is adjustably attached to the upper brace structure and extends distally from the hard shell to a location below the foot.

A fourth aspect of the present invention concerns an ankle brace configured to provide support of the ankle joint between the leg and foot. The ankle brace broadly includes an upper brace structure and an elongated strap. The upper brace structure is configured to be attached to the leg and anchor the ankle brace above malleoli of the joint. The elongated strap is adjustably attached to the upper brace structure. The elongated strap is dimensioned and configured to extend distally from the upper brace structure to a location below the foot. The elongated strap includes a flexible fabric strip that presents opposite faces. The elongated strap includes a high-friction coating applied to at least one of the faces and extends to the location. The faces exhibit a strip self-coefficient of friction and the coating exhibits a coating self-coefficient of friction greater than the strip self-coefficient of friction, with the coating thereby configured to secure the elongated strap at the location and restrict strap movement relative to the foot.

Other aspects and advantages of the present invention will be apparent from the following detailed description of the preferred embodiments and the accompanying drawing figures.

BRIEF DESCRIPTION OF THE DRAWING FIGURES

Preferred embodiments of the invention are described in detail below with reference to the attached drawing figures, wherein:

FIG. 1 is a lateral side elevation of an ankle stabilizer constructed in accordance with a preferred embodiment of the present invention, showing the ankle stabilizer secured around a lower leg, foot, and ankle of a user, where the ankle stabilizer includes a compressive sheath, lateral and medial stabilizing straps wrapped around the sheath, a U-shaped heel plate secured by a lateral one of the straps, and a proximal cuff secured around the sheath and straps, with the ankle stabilizer being anchored above the lateral and medial malleoli of the ankle by the sheath and below the malleoli by the heel plate;

FIG. 2 is a posterior elevation of the ankle stabilizer shown in FIG. 1, showing stabilizing straps tensioned and removably attached to sides of the sheath, and also showing lateral and medial upright walls of the heel plate flexed inwardly by the tensioned lateral strap;

FIG. 3 is an anterior perspective of the ankle stabilizer shown in FIGS. 1 and 2, showing proximal strap ends of the stabilizing straps attached to a tubular sleeve of the sheath adjacent a rear margin of the sleeve, and showing distal strap ends detached from the sheath, with the straps being unwound from the foot in an unsecured strap configuration and the heel plate slidably received on the lateral strap, and further showing the proximal cuff unwound from the sheath;

FIG. 4 is a posterior perspective of the ankle stabilizer shown in FIGS. 1-3, showing the stabilizing straps in the unsecured strap configuration;

FIG. 7 is an anterior perspective of the ankle stabilizer shown in FIGS. 1-6, showing the lateral and medial straps wrapped around the sheath in the secured strap configuration, with the heel plate being secured over the sheath and medial strap, and with the lateral strap being wrapped over and securing the heel plate;

FIG. 8 is an anterior perspective of the ankle stabilizer shown in FIGS. 1-7, showing the lateral and medial straps wrapped around the sheath in the secured strap configuration, and also showing the proximal cuff wrapped around the sheath and distal strap ends to further secure the strap and anchor the ankle stabilizer about the leg;

FIG. 9 is a bottom view of the ankle stabilizer shown in FIGS. 1-8, showing the heel plate anchored below and secured to the foot by the secured lateral strap;

Figure 12:
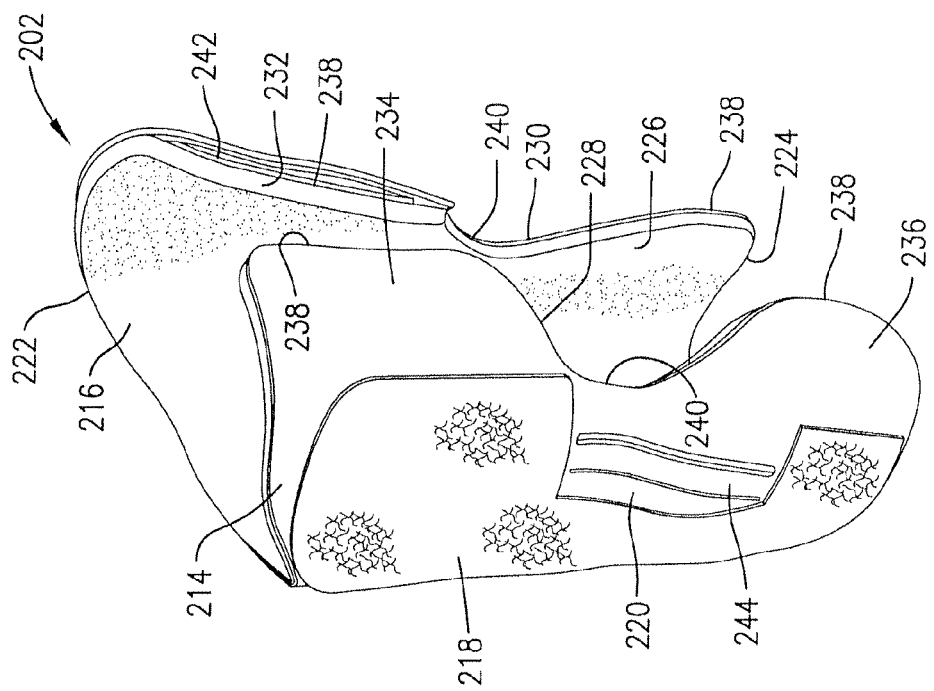
Figure 11:
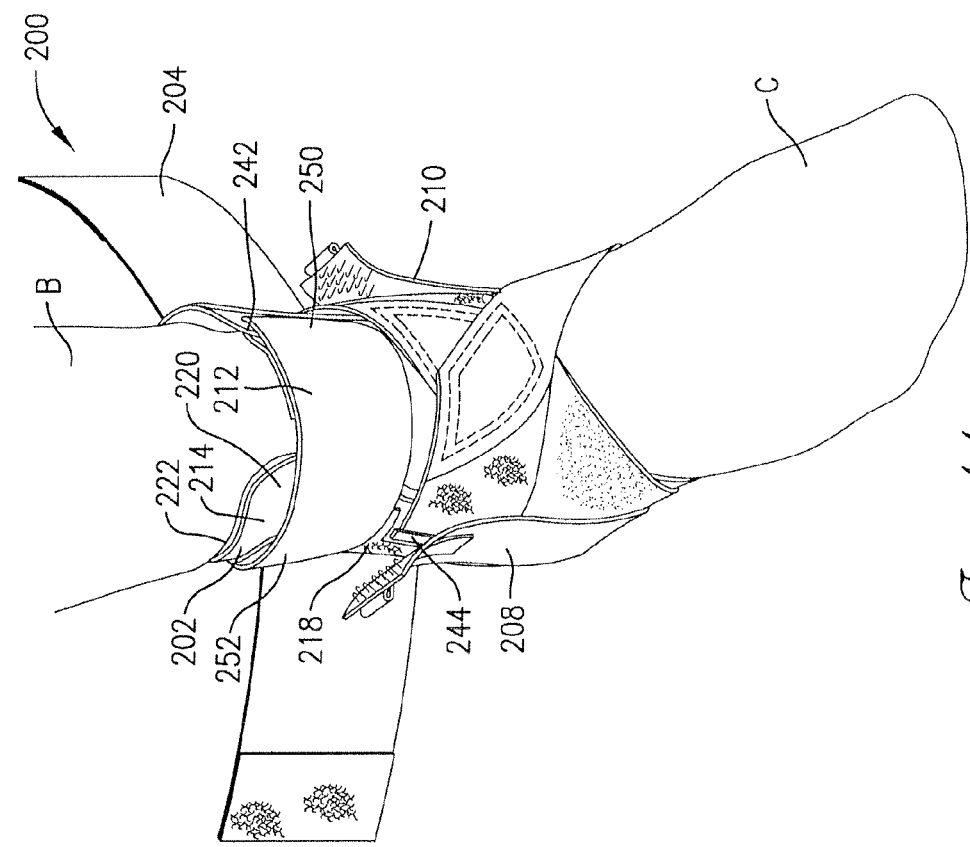
Figure 16:
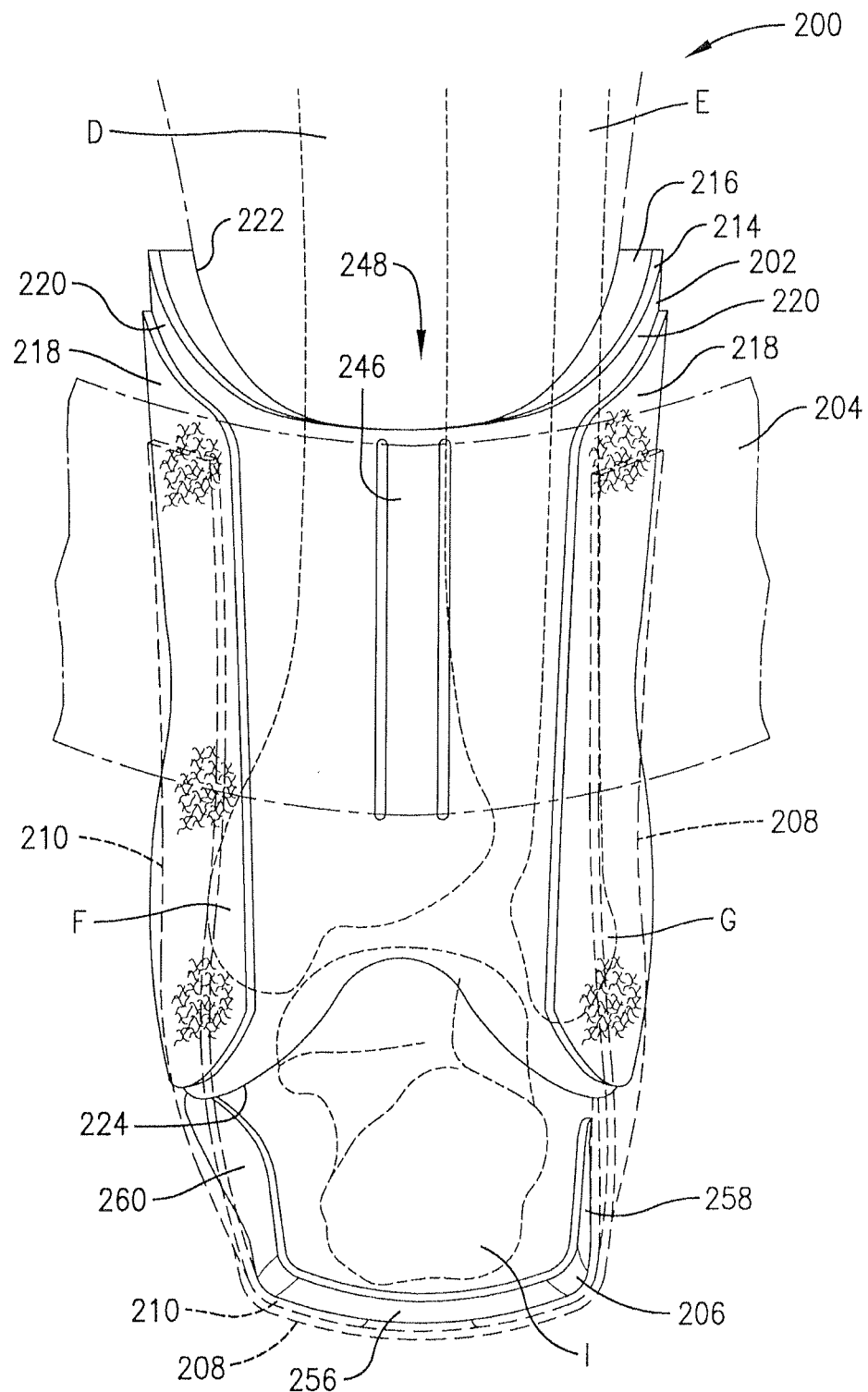

FIG. 10 is an aft side elevation of the lateral strap shown in FIGS. 1-9, showing a distally and diagonally extending body and a proximal, generally horizontal strap extension, with the body including a fabric strip that presents opposite faces covered by a high-friction coating, with the coating extending continuously along the faces between an overlapping area of the body and strap extension and a distal fastener strip attached to a distal end of the body;

FIG. 11 is an anterior perspective of an ankle stabilizer constructed in accordance with a second preferred embodiment of the present invention, and showing a high-ankle support, lateral and medial stabilizing straps wrapped and secured to the support in a secured strap configuration, a closure strip attached to the support in a secured strip position adjacent a proximal end of the support, and a top cuff of the ankle stabilizer attached to the support in an unwound position;

FIG. 12 is an enlarged anterior perspective of the high-ankle support shown in FIG. 11, showing a substantially rigid outer shell, an inner padding attached to an inner surface of the shell, and loop fastener strips attached to opposite sides of the outer shell, with the shell including oppositely positioned strap connectors;

FIG. 13 is a fragmentary anterior perspective of the ankle stabilizer shown in FIG. 11, showing the stabilizing straps unwound from the high-ankle support in an unsecured strap configuration, with a U-shaped heel plate slidably attached to the medial stabilizing strap, and showing one end of the closure strip detached from the support;

FIG. 14 is a fragmentary anterior perspective of the ankle stabilizer shown in FIGS. 11 and 13, showing the medial stabilizing strap wrapped and secured to the support in the secured strap configuration and the lateral stabilizing strap in the unsecured strap configuration, with the closure strip attached and secured at both ends thereof to the support in the secured strip position;

FIG. 15 is a fragmentary lateral side elevation of the ankle stabilizer shown in FIGS. 11, 13, and 14, showing the ankle stabilizer secured around an ankle, with the high-ankle support covering lateral and medial malleoli of the ankle, and showing the stabilizing strips in the secured strap configuration, with both straps engaging and flexing upright walls of the heel plate; and FIG. 16 is a fragmentary posterior elevation of the ankle stabilizer shown in FIGS. 11 and 13-15, showing the stabilizing strips in the secured strap configuration, with both straps engaging and flexing the upright walls, and showing the top cuff of the ankle stabilizer attached to the support in the unwound position.

The drawing figures do not limit the present invention to the specific embodiments disclosed and described herein. The drawings are not necessarily to scale, emphasis instead being placed upon clearly illustrating the principles of the preferred embodiment.

DETAILED DESCRIPTION OF THE PREFERRED EMBODIMENTS

Figure 1:
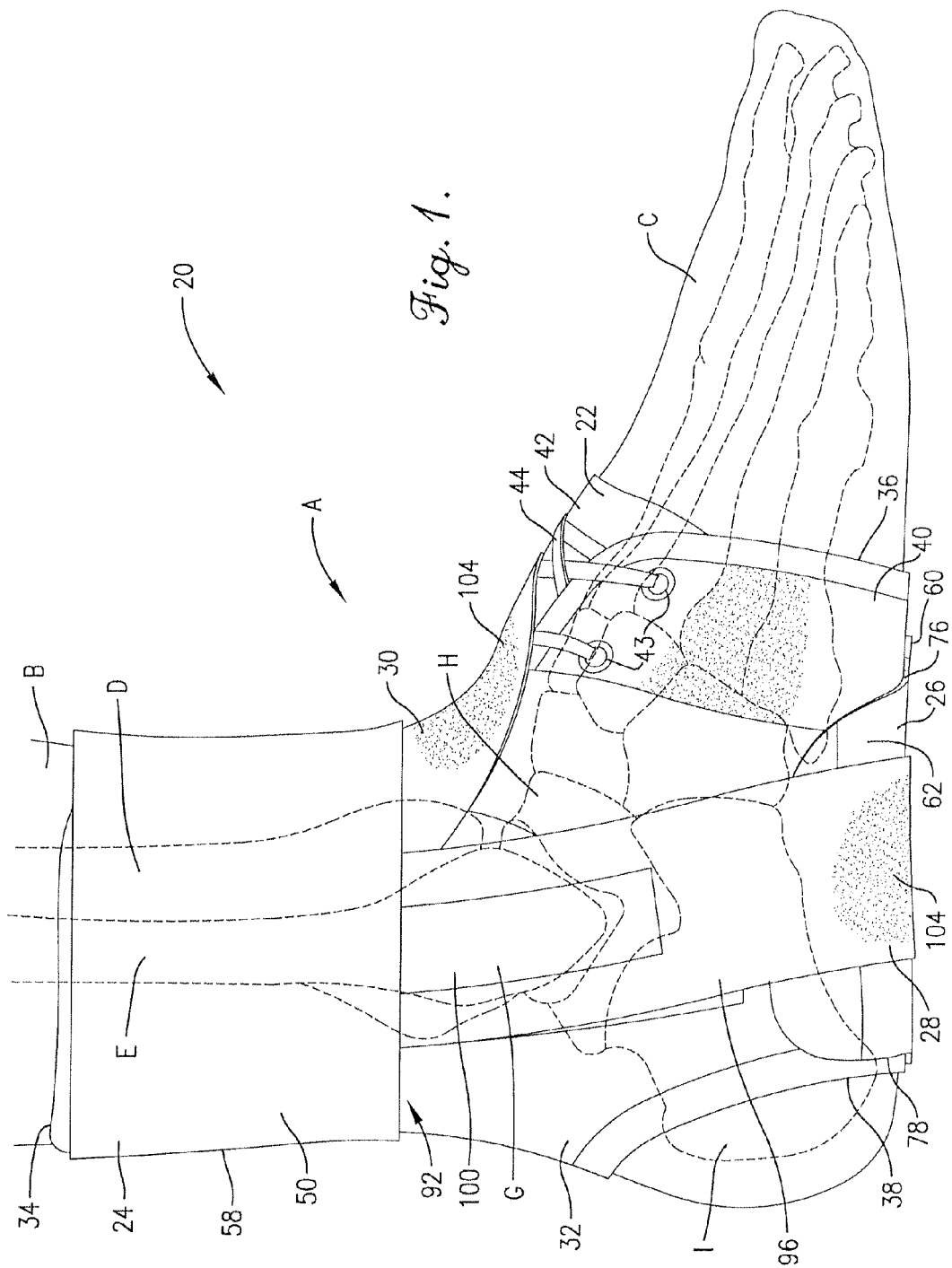
Figure 2:
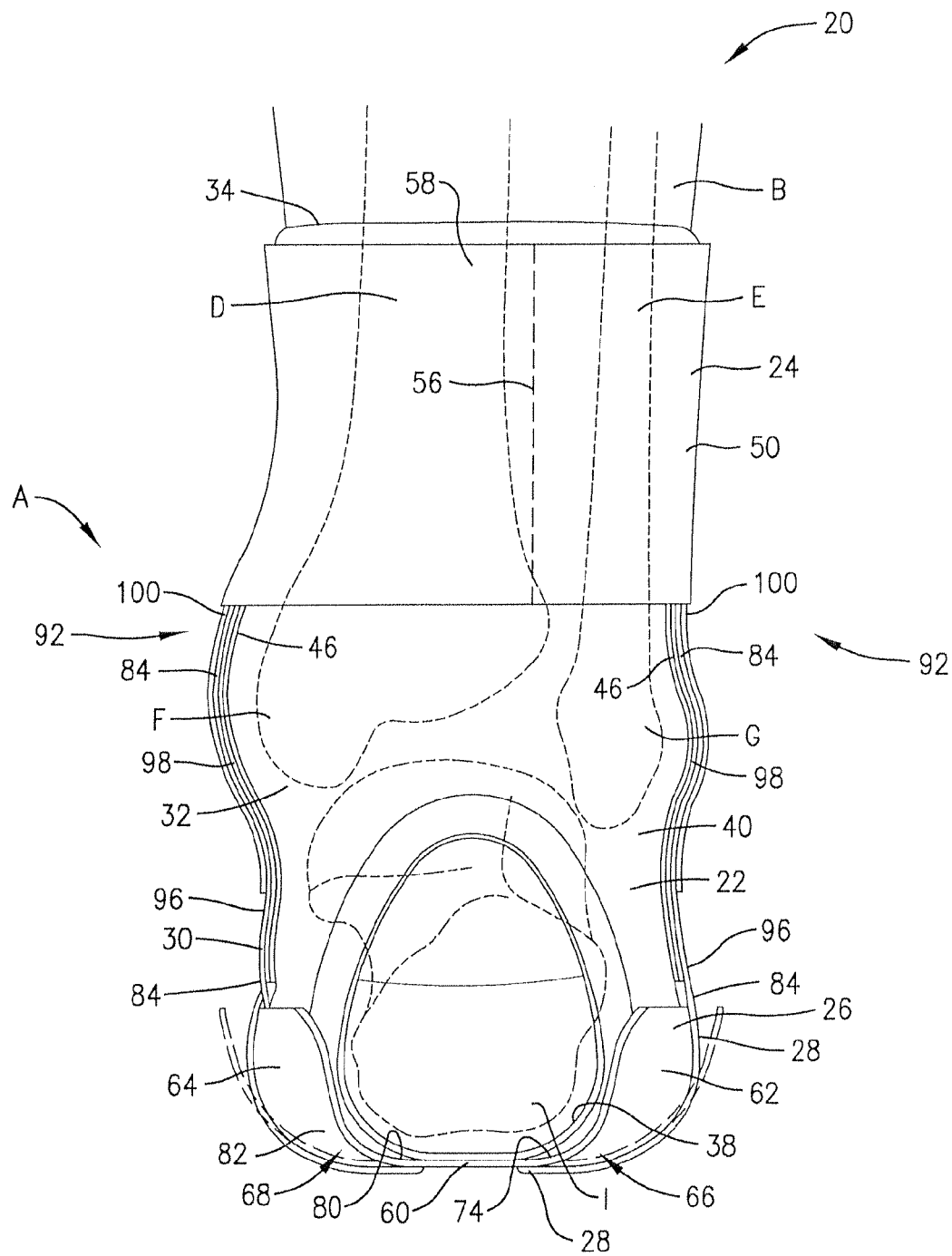

Turning initially to FIGS. 1 and 2, a synovial ankle joint A of the human body is generally formed between the leg B and the foot C. The ankle joint A includes a number of bones that generally connect the foot C to the tibia D and fibula E of the leg B. For instance, the tibia D and fibula E present corresponding medial and lateral malleoli F,G that are attached to the talus H and calcaneous I. The ankle joint A is flexible in a number of directions including inversion (where the foot is turned inwardly relative to the leg and which can result in undue stretching of lateral ligaments), eversion (where the foot is turned outwardly relative to the leg and which can result in undue stretching of medial ligaments), dorsiflexion (where the anterior end of the foot is turned upwardly relative to the heel) and plantar flexion (where the anterior end of the foot is turned downwardly relative to the heel). Although several foot joints adjacent the heel permit these movements, the words "ankle joint" as used herein will generally refer to the bone and ligament structure which permits up, down, inward (i.e., medial), or outward (i.e., lateral) movement of the foot C relative to the leg B.

Ankle sprains and other injuries associated with the ankle joint A involve excessive inversion, which often causes over-extension of laterally positioned tissues, such as the anterior and posterior talofibular ligaments and the calcaneofibular ligament (all not shown). Other ankle injuries involve excessive eversion, which can cause over-extension of medially positioned tissues, such as the deltoid ligament (not shown). Yet further, some ankle injuries can result in damage to tissues above the ankle, such as over-extension of the syndesmotic ligament (this type of injury is commonly referred to as a high ankle sprain).

A removable ankle stabilizer 20 is constructed and configured to provide lateral and medial support of the ankle joint A with a selective degree of immobilization of the joint. More particularly, the ankle stabilizer 20 is operable to permit a progressive reduction of joint immobilization of the joint during rehabilitation. In this manner, the ankle stabilizer 20 allows strengthening of various muscles while injured tissues (e.g., muscles, tendons, ligaments) of the joint heal and return to normal activity. Most notably, the ankle stabilizer 20 has been found to permit a significant amount of dorsiflexion and plantar flexion of the foot, and this also been discovered to allow strengthening of muscles during ankle rehabilitation and to prevent atrophy of tissue in and around the ankle.

The removable ankle stabilizer 20, selected for illustration, is also configured to provide compression of the foot C, lower leg B, and ankle to minimize swelling of tissues. Thus, the ankle stabilizer 20 is advantageously configured to provide support, stabilization, and immobilization of the ankle joint A during the acute and rehabilitative stages of injuries associated with the ankle joint A. It will be appreciated that the principles of the present invention are equally applicable with respect to support, stabilization, and immobilization of other types of synovial joints that experience injury to bones, ligaments, muscles, tendons, or other tissues. The ankle stabilizer 20 broadly includes a pliable lace-up sheath 22, a compressive proximal cuff 24, a U-shaped heel plate 26, and lateral and medial stabilizing straps 28,30.

Turning to FIGS. 1-4, the sheath 22 provides compression of the lower leg B and foot C and serves to anchor the ankle stabilizer 20 proximally above malleoli F,G, as will be discussed in greater detail. The sheath 22 includes a boot-shaped, tubular sleeve 32 that presents proximal and distal openings 34,36, and a heel opening 38. As used herein, the term "proximal" generally refers to a location along the leg B and foot C that is relatively close to the upper leg, and the term "distal" generally refers to a location along the leg B and foot C that is relatively far from the upper leg. The sleeve 32 also includes a sleeve body 40 and a stretchable elastic tongue 42. The sleeve body 34 presents a forwardly facing open face that extends from the proximal opening 34 to the distal opening 36. The illustrated sleeve 32 is preferably made of fabric that includes one or more synthetic materials, such as nylon or neoprene. The sleeve body 34 also presents a plurality of apertures 43 spaced along the length of the open face and receive a lace 44 of the sheath 22, with the lace 44 being secured to tighten the sheath 22 about the ankle joint A. The sheath 22 also includes loop fastener strips 46 attached to lateral and medial sides 48 of the sheath 22. As used herein, the terms "loop fastener" and "hook fastener" generally refer to corresponding fasteners of a conventional hook-and-loop arrangement. The loop fastener strips 46 preferably extend distally from adjacent the proximal opening 34 to a location adjacent the heel opening 38.

The sheath 22 is slipped onto the ankle joint A by inserting the foot C into the proximal opening 34 and sliding the sheath 22 up the foot C until the foot C extends through the distal opening 36 and the heel of the foot C is received by the heel opening 38, with the tongue 42 lying on top of the foot C. With the foot C received in the sheath 22, the tongue 42 stretches so that the sheath 22 expands accordingly and is snugly received about the foot C, leg B, and ankle. Thus, the sheath 22 is tensioned about the ankle and holds itself in place as the lace 44 is tightened to further constrict the sheath 22. The elastic tongue 42 is also configured to cover the top of the foot C and prevent chafing of the lower leg B and foot C. While the sheath 22 preferably is secured by the lace 44, it is also within the scope of the present invention where another type of fastener secures the sheath 22 to provide compression of the foot C and leg B. Features of another preferred tubular sleeve that provides compression and thereby reduces swelling of a sprained ankle are disclosed in U.S. Pat. No. 6,126,625, issued Oct. 3, 2000, entitled ORTHOTIC DEVICE FOR A JOINT OF THE HUMAN BODY, which is hereby incorporated in its entirety by reference herein.

The illustrated sheath 22 is preferably entirely pliable to provide a comfortable fit and uniform compression of the foot C and leg B. However, it is also within the scope of the present invention where the sheath 22 includes rigid components that provide additional support to the ankle joint A. For instance, the sleeve 32 could include rigid bars or plates integrated into the sleeve body 40 and positioned along the sides 48 to provide additional support against inversion and/or eversion of the foot C. The illustrated sheath 22 preferably permits the normal full range of dorsiflexion and plantar flexion of foot C. However, for some aspects of the present invention, the sheath 22 could restrict at least some dorsiflexion and plantar flexion of the foot C.

Again turning to FIGS. 1-4, the proximal cuff 24 is operable to provide additional compression of the lower leg B and to further anchor the stabilizer 20 to the leg B and above malleoli F,G. The cuff 24 includes an elastic strip 50 with opposite cuff sections and hook and loop fasteners 52,54 stitched onto respective cuff sections. The illustrated cuff 24 is preferably attached to the sleeve 32 by a line of stitching 56 extending along a rear margin 58 of the sheath 22, with the respective cuff sections extending in lateral and medial directions from the stitching 56. The fasteners 52,54 are attached to corresponding sides of the strip 50 so that the fasteners 52,54 can be adjustably secured to each other once the cuff sections are wrapped forwardly about the leg B. Thus, the cuff 24 is adjustably tensionable about the leg B. The cuff 24 is positioned just below the proximal opening 34 and is configured to wrap partly around the straps 28,30 and the lace 44 (see FIG. 8). The stabilizer 20 also preferably includes the illustrated cuff 24 in order to provide adjustable compression about the lower leg B (in addition to the compression provided by the sheath 22). The cuff 24 also is preferably used to further anchor the stabilizer 20 above malleoli F,G. For some aspects of the present invention, the stabilizer 20 could include an alternative cuff configuration or could be used without the cuff 24.

Turning to FIGS. 1-6 and 9, the heel plate 26 is secured below the sheath 22 by stabilizing straps 28,30 that are adjustably tensionable, as will be discussed in greater detail. Furthermore, the heel plate 26 is configured to conform to the foot C and serves to anchor the ankle stabilizer 20 below the foot C and the malleoli F,G. The illustrated heel plate 26 preferably comprises a unitary molded synthetic resin construction, and could be made of one or more types of elastomers (e.g., a thermoplastic elastomer (TPE) or thermoplastic vulcanizate (TPV)) or plastic materials (e.g., polyurethane, PVC, polyethylene, etc.). More preferably, the synthetic resin material comprises a Santoprene™ TPV, manufactured by ExxonMobil Chemical of Houston, Tex. The preferred Santoprene™ heel plate material also preferably has a Shore-A Hardness that ranges from about 70 to about 100. In addition, the heel plate 26 is made of a material that is harder and more rigid than the material of the pliable straps 28,30. In this manner, the heel plate 26 is constructed to provide a resilient and secure anchoring structure that can be retained below the foot C.

The heel plate 26 includes a base plate 60 and upright lateral and medial walls 62,64 that extend generally along a longitudinal direction. The walls 62,64 also extend upwardly from side margins of the base plate so that the walls 62,64 and base plate 60 cooperatively present a U-shaped cross section, with lateral and medial bend regions 66,68 that extend longitudinally and are presented between the base plate 60 and walls 62,64 (see FIGS. 2 and 5). The base plate 60 also presents centrally positioned lateral and medial longitudinal slots 70,72 that are elongated and present enlarged slot ends. The slots 70,72 slidably receive one of the straps 28,30, as will be discussed further (see FIGS. 5 and 6).

Figure 5:
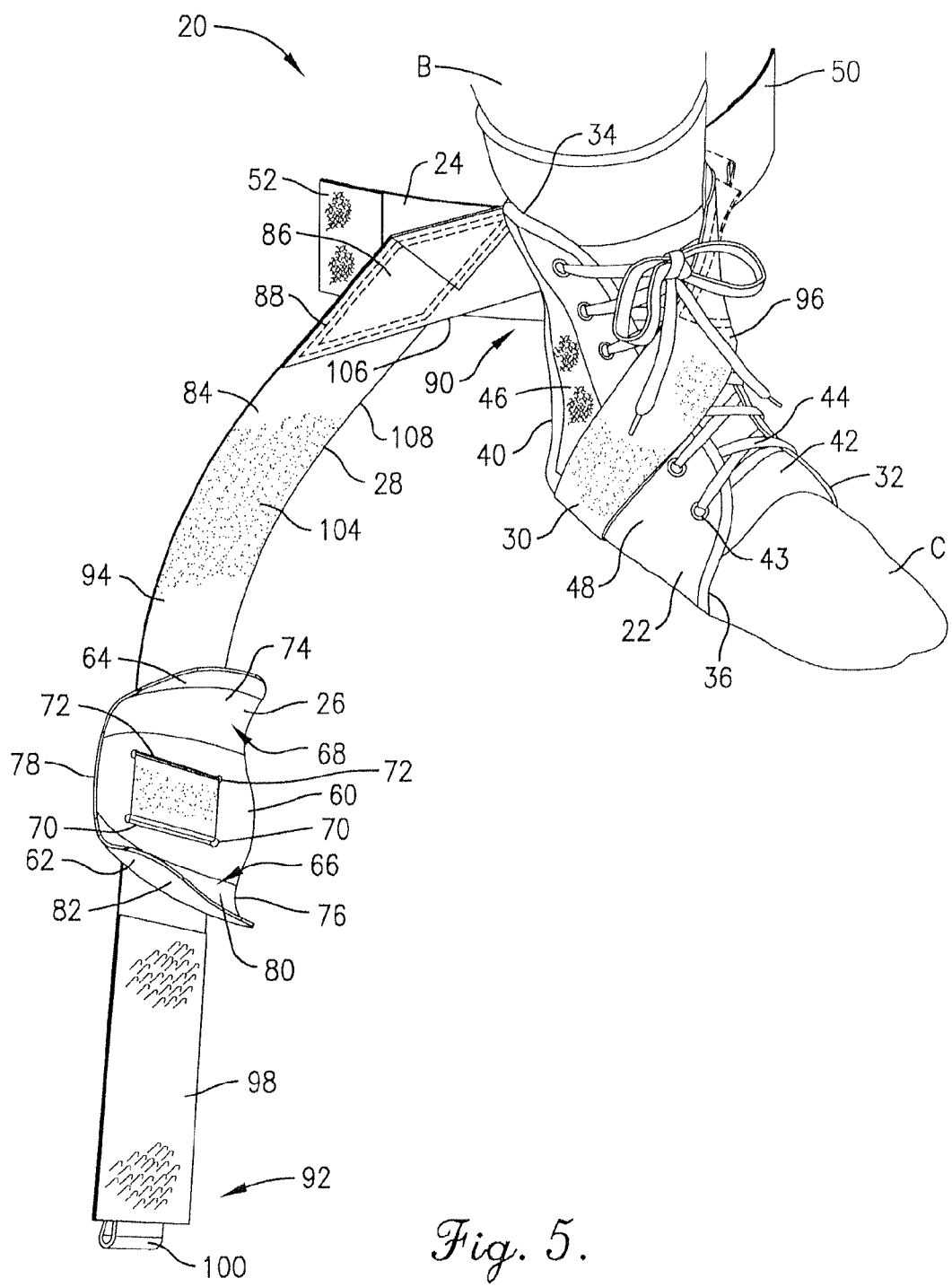
FIG. 5 is an anterior perspective of the ankle stabilizer shown in FIGS. 1-4, showing the medial strap wrapped and secured around the sheath in a secured strap configuration, with the medial distal strap end removably attached to a medial side of the sheath, with the lateral strap in the unsecured strap configuration.
Figure 6:
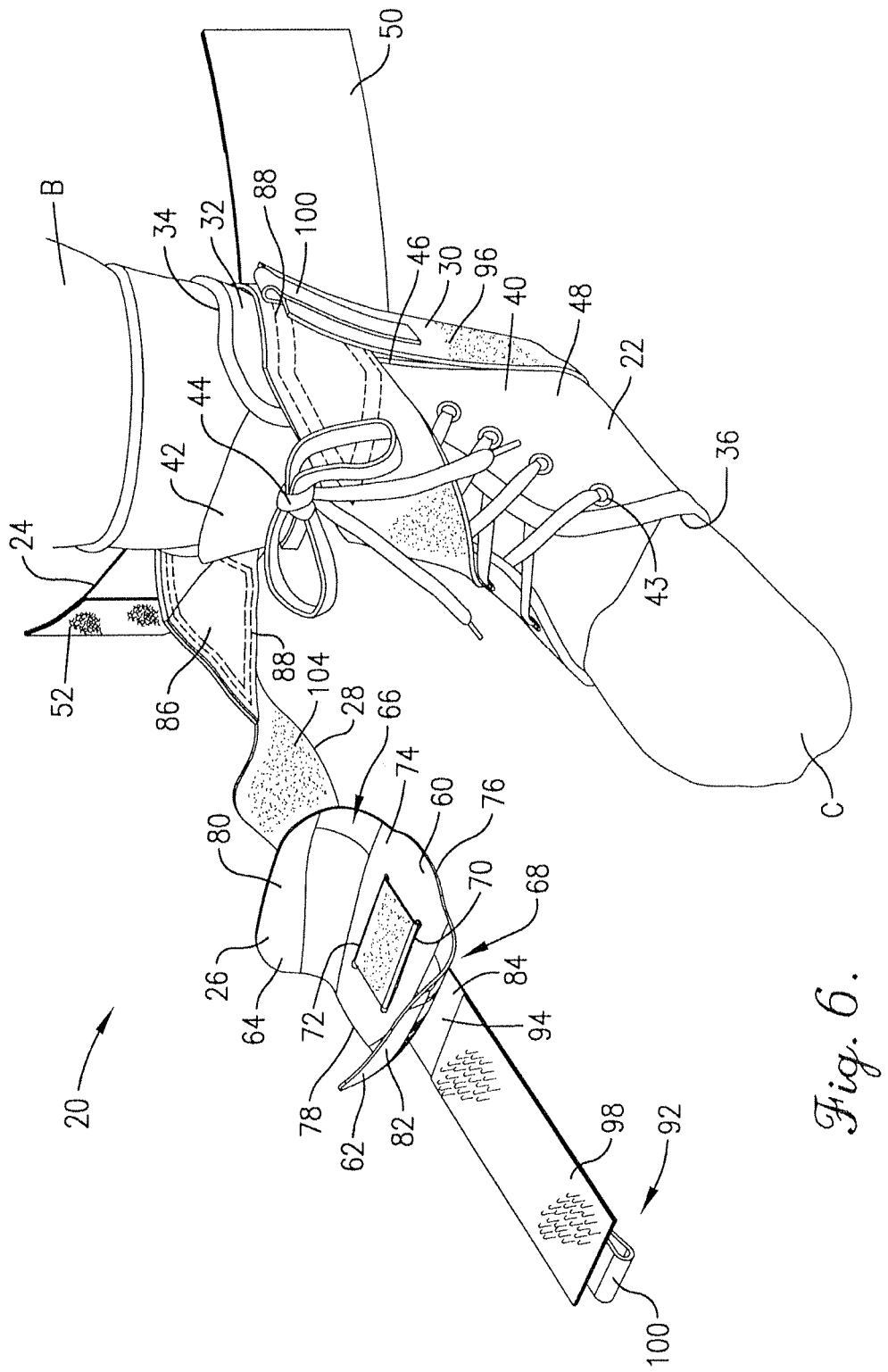
FIG. 6 is an anterior perspective of the ankle stabilizer shown in FIGS. 1-5, showing a medial side of the sheath, with the medial strap wrapped around the sheath in the secured strap configuration and the lateral strap in the unsecured strap configuration.

Turning to FIGS. 2, 5, and 6, the base plate 60 and walls 62,64 preferably present a longitudinal channel 74 that extends continuously between anterior and posterior open ends 76,78, and the channel 74 is also preferably devoid of any walls that extend upwardly from the base plate 60. The channel 74 is configured to receive the bottom of the foot C adjacent the heel, with the heel extending rearwardly from the posterior open end 78 and an anterior part of the foot C extending forwardly of the anterior open end 76 (see FIG. 1). Importantly, the open channel configuration of the heel plate 26 permits the foot C to be selectively positioned in the heel plate 26 along the longitudinal direction so that the heel plate 26 can adjustably conform to different foot shapes while being comfortable to wear. Specifically, this configuration allows walls 62,64 and base plate 60 to flex from a relaxed plate configuration (shown in broken lines in FIG. 2) about a longitudinal axis of the heel plate 26 to assume a flexed plate configuration that conforms to the foot C (see FIG. 2). Preferably, the heel plate 26 presents a thickness between inner and outer plate surfaces 80,82 that ranges between about 0.020 inches and about 0.200 inches to allow movement between the relaxed and flexed configurations while providing desired plate rigidity and strength.

The illustrated heel plate 26 is configured to be positioned below the foot C and malleoli F,G and serve as a distal anchor of the ankle stabilizer 20. It has been found that the construction of the heel plate 26 also permits the heel plate 26 to be comfortably and adjustably applied to various foot shapes while providing a resilient and substantially rigid anchoring structure beneath the ankle joint A. However, for some aspects of the present invention, the ankle stabilizer 20 could be applied to an injured ankle without the heel plate 26 and still provide sufficient support to the ankle joint A, e.g., where the straps 28,30 themselves serve to anchor the ankle stabilizer 20 below the foot C and malleoli F,G.

The heel plate 26 is preferably positioned outside of the sheath 22, i.e., the sleeve 32 is received in the channel 74 and engages the inner surface 80 of the heel plate 26. However, the principles of the present invention are applicable where the heel plate 26 is secured within the tubular internal passage presented by the sleeve 32 or is integrally constructed as part of and secured within the sleeve 32.

Turning to FIGS. 2-10, the straps 28,30 are adjustably tensionable, serve to provide adjustable compression of the ankle, leg B, and foot C, and restrict inversion and/or eversion of the foot C. In particular, the straps 28,30 serve to adjustably interconnect the proximal anchoring structure (e.g., the sheath 22) and the distal anchoring structure (e.g., the heel plate 26) and thereby stabilize the ankle joint A. The illustrated straps 28,30 are mirror images of one another and are otherwise identical in construction. The straps 28,30 each include a fabric strap body 84 and a proximal fabric extension 86 that overlap one another and are attached to each other with stitching 88 along an overlapping strap area. However, the principles of the present invention are applicable where the strap body 84 and extension 86 comprise a unitary piece of fabric. As will be discussed, the strap body 84 and extension 86 are joined with an obtuse angle therebetween. The extension 86 and strap body 84 preferably comprise a synthetic nylon fabric material, but could include another synthetic material without departing from the scope of the present invention. The extension 86 and strap body 84 present respective proximal and distal strap ends 90,92 of the straps 28,30.

The extension 86 and strap body 84 also cooperatively present opposite fore and aft strap faces 94,96 (see FIGS. 3 and 4). As will be shown, the straps 28,30 are wrapped about the sheath 22 so that fore strap faces 94 face generally inwardly to engage the sheath 22 and the aft strap faces 96 face generally outwardly away from the sheath 22. The straps 28,30 each include a hook fastener strip 98 attached to the fore strap face 94 with stitching 99 and a looped tab 100 attached to the aft strap face 96, with both the hook fastener strip 98 and looped tab 100 being attached to the strap body 84 adjacent the distal strap end 92 (see FIGS. 3, 4, and 10). The straps 28,30 also include a loop fastener strip 102 attached to the aft strap face 96 of the extension 86 adjacent the proximal strap end 90 (see FIGS. 4 and 10).

The straps 28,30 also include a high-friction coating 104 applied in a thin layer to both of the fore and aft strap faces 94,96 of the strap body 84 and applied so that the layer extends continuously from the overlapping strap area to the hook fastener strip 98 (see FIGS. 3, 4, and 10). However, it is also within the ambit of the present invention where the high-friction coating 104 is applied in a pattern (e.g., where the material is applied as a uniform pattern of spaced apart dots or strips along the strap face) between the overlapping strap area and the hook fastener strip 98. It will be appreciated that the illustrated layer of coating 104 can be applied using various conventional techniques, such as dipping, screen-printing, spraying, or brushing. While the illustrated straps 28,30 preferably have coating 104 on both faces 94,96, for some aspects of the present invention the coating 104 could be applied to only one of the faces 94,96. As will be discussed, the coating 104 is configured to promote frictional interengagement between components of the ankle stabilizer 20. The high-friction coating 104 preferably comprises an elastic material that includes at least one of latex, natural rubber, synthetic rubber, urethane, and neoprene. More preferably, the elastic material comprises the synthetic rubber coating identified by the trade name "Plasti Dip," and manufactured by Plasti Dip International of 3920 Pheasant Ridge Drive•Blaine, Minn. 55449. Preferably, the coating 104 exhibits a self-coefficient of friction that is greater than a self-coefficient of friction of the fabric strap faces 94,96. The term "self-coefficient of friction" as used herein refers to the coefficient of friction associated with frictional engagement between a pair of structures that comprise the same material. More preferably, the coating 104 exhibits a self-coefficient of friction greater than about 0.2 in order to provide the desired frictional interengagement.

As mentioned previously, the extension 86 and strap body 84 are preferably positioned and joined to one another at an angled joint, with a downward angle θ therebetween that is measured between respective adjacent margins 106,108. The angle θ preferably comprises an obtuse angle (see FIG. 10). More preferably, the angle θ ranges between about 130 degrees and about 150 degrees. As will be shown, the angled joint between the extension 86 and strap body 84 allows the straps 28,30 to be secured while allowing dorsiflexion and plantar flexion.

For the lateral strap 28, the extension 86 projects in a medial direction from the strap body 84, when viewing the aft strap face 96 (see FIGS. 4 and 10). Conversely, the extension 86 of the medial strap 30 projects in a lateral direction from the strap body 84, when viewing the aft strap face 96. For both straps 28,30, the margin 106 of the extension 86 presents a length L that ranges between about one (1) inch and about six (6) inches and, more preferably, is about three (3) inches (see FIG. 10). For some aspects of the present invention, the construction and arrangement of strap body 84 and extension 86 could be alternatively configured without departing from the scope of the present invention.

Turning to FIGS. 3-8, the illustrated straps 28,30 are stitched to the sleeve 32 at attachment locations 110 adjacent the proximal opening 34 of the sleeve 32 and adjacent the rear margin 58 (see FIG. 4). The lateral strap 28 extends in a lateral direction from the sleeve 32 and the medial strap 30 extends in a medial direction from the sleeve 32 when the straps 28,30 are unwrapped and in an unsecured strap configuration (see FIGS. 3 and 4). As the straps 28,30 are wrapped and secured around the sheath 22 into a secured strap configuration, the extensions 86 project generally forwardly and horizontally about the sheath 22 from the attachment locations 110 (see FIG. 6). The strap body 84 of the medial strap 28 extends from the extension 86 distally and laterally across the tongue 42 and along the lateral side 48 of the sheath 22 (see FIGS. 5 and 6). That is, the strap body 84 extends from the angled joint, which is spaced forwardly from the attachment location 110, at the downward angle θ from the extension 86. In this manner, the strap body 84 is positioned away from the top of the foot C to permit dorsiflexion. The strap body 84 of the medial strap 28 then wraps underneath the bottom of the sleeve 32 and extends proximally along the medial side 48 of the sheath 22, with the hook fastener strip 98 removably attached to the medial loop fastener strip 46.

Conversely, the strap body 84 of the lateral strap 30 extends from the respective extension 86, distally and laterally across the tongue 42 and along the medial side 48 of the sheath 22 (see FIGS. 7 and 8). In particular, the strap body 84 of the lateral strap 30 extends from the corresponding angled joint, which is spaced forwardly from the respective attachment location 110, at the downward angle θ relative to the extension 86. The strap body 84 of the lateral strap 30 then wraps underneath the bottom of the sleeve 32 and extends proximally along the lateral side 48 of sheath 22, with the hook fastener strip 98 removably attached to the lateral loop fastener strip 46. Thus, both straps 28,30 are attached by a hook-and-loop fastener arrangement that permits adjustable tensioning of the straps 28,30.

The proximal cuff 24 is configured to be wrapped about the sheath 22 and the secured straps 28,30 so that the proximal cuff 24 covers and frictionally engages the attached distal strap ends 92, portions of the straps 28,30 adjacent the overlapping strap areas, the tongue 42, and the lace 44. In this manner, the cuff 24 serves to restrict inadvertent detachment of the distal strap ends 92 and serves to further anchor the ankle stabilizer 20 about the leg B and above malleoli F,G. However, for some aspects of the present invention, the ankle stabilizer 20 could be devoid of cuff 24.

The illustrated straps 28,30 are preferably configured and attached to the sheath 22 to permit at least some dorsiflexion and plantar flexion of the foot C. The extensions 86 serve to position the strap body 84 at a location spaced from the distal opening 36. More particularly, the extensions 86 each project in a generally horizontal and forward direction about the sleeve 32 to position a proximal end of the strap body 84 forwardly of the rear margin 58 and adjacent the tongue 42. As a result, the straps 28,30 are configured so that the respective strap body 84 is directed distally and laterally from the extension 86, about the leg B, and onto the opposite side of the sheath 48. In this manner, the straps 28,30 are restricted from applying significant downward pressure onto the top of the foot C, and the ankle stabilizer 20 thereby allows dorsiflexion and plantar flexion.

The straps 28,30 are preferably tensioned to provide additional compression of the leg B, foot C, and ankle. Furthermore, the straps 28,30 are tensioned to support and stabilize the ankle joint A. For example, the lateral strap 28 generally supports the lateral side of the ankle joint A and restricts inversion. While the lateral strap 28 is preferably attached adjacent the lateral side 48, wraps around the medial side 48, and is attached to the lateral loop fastener strip 46, it is also within the ambit of the present invention where the lateral strap 28 is configured alternatively to provide support along the lateral side of the ankle joint A. Preferably, alternative configurations of the lateral strap 28 include a tensioned strap with one portion attached to a location adjacent the proximal opening 34 (such as the lateral loop fastener strip 46) and another portion secured to a location on the heel plate 26 (or otherwise secured at a location below the foot C) so that the tensioned strap restricts movement of the locations away from each other (such as would occur during inversion of the foot C). For instance, an alternative configuration of the lateral strap 28 could comprise a strap that is not wrapped around the sheath 22 but simply extends directly from the heel plate 26 to the lateral loop fastener strip 46.

Similarly, the medial strap 30 generally supports the medial side of the ankle joint A and restricts eversion. Although the medial strap 30 also preferably wraps around the sheath 22, it is within the ambit of the present invention where the medial strap 30 is alternatively configured to provide support along the medial side of the ankle joint A. Alternative configurations of the medial strap 30 preferably include a tensioned strap with one portion attached to a location adjacent the proximal opening 34 (such as the medial loop fastener strip 46) and another portion secured to a location on the heel plate 26 (or otherwise secured at a location below the foot C) so that the tensioned strap restricts movement of the locations away from each other (such as would occur during eversion of the foot C). For instance, an alternative configuration of the medial strap 30 could comprise a strap that is not wrapped around the sheath 22 but simply extends directly from the heel plate 26 to the medial loop fastener strip 46.

By supporting the respective sides of the ankle joint A to restrict inversion and eversion, the lateral and medial straps 28,30 serve to mimic tissues that control inversion and eversion, such as the peroneus brevis muscle and associated tendons. Additional details concerning these tissues are disclosed in the above-incorporated '625 patent.

As discussed, the straps 28,30 also include coatings 104 to restrict relative movement between components of the ankle stabilizer 20. For example, the coated straps 28,30 each engage the sheath 22 along the coating 104 (see FIGS. 5-9). In this manner, the straps 28,30 are restricted from moving relative to the sheath 22 when wrapped and secured about the sheath 22 in the secured strap configuration. Preferably, the straps 28,30 at least partly engage each other so that coatings 104 of respective straps 28,30 are in frictional engagement and thereby restrict relative movement between the straps 28,30 (see FIGS. 7 and 8). The straps 28,30 are preferably secured by wrapping the medial strap 30 around the sheath 22 and then wrapping the lateral strap 28 on top of the medial strap 30 and around the sheath 22. However, the principles of the present invention are applicable where the lateral strap 28 is wrapped first, followed by the medial strap 30.

In the illustrated embodiment, the lateral strap 28 slidably receives the heel plate 26 by extending the distal strap end 92 through the slots 70,72. Preferably, the distal strap end 92 is fed from the outer surface 82 through the medial slot 72, through the channel 74, and through the lateral slot 70. In this manner, the lateral strap 28 is adjustably attached to the heel plate 26 and secures the heel plate 26. More particularly, the lateral strap 28 engages the outer surface 82 along both of the walls 62,64. Consequently, as the lateral strap 28 is secured and tensioned, the lateral strap 28 engages the walls 62,64 and flexes the heel plate 26 (by flexing the walls 62,64 and base plate 60) securely around the foot C (see FIG. 2). The medial strap 30 is wrapped between the sheath 22 and the heel plate 26. However, it is also within the scope of the present invention where the medial strap 30 is wrapped around the heel plate 26 so that both straps 28,30 engage the outer surface 82 of walls 62,64 to generally flex the heel plate 26, e.g., where more force is required to conform the heel plate 26 to the foot C. The principles of the present invention are also applicable where the medial strap 30 is slidably attached to the heel plate 26.

As discussed, the straps 28,30 include high-friction coatings 104 that promote frictional engagement between the straps 28,30 and between each strap 28,30 and the sheath 22. In addition, the coatings 104 also serve to promote frictional engagement between each strap 28,30 and the heel plate 26. For instance, coating 104 applied to the fore strap face 94 of the lateral strap 28 engages the outer plate surface 82, particularly along walls 62,64, to restrict relative movement between the heel plate 26 and lateral strap 28. Similarly, coating 104 applied to the aft strap face 96 of the medial strap 30 engages the inner plate surface 80 to restrict relative movement between the heel plate 26 and the medial strap 28. Consequently, the straps 28,30 and heel plate 30 are frictionally interengaged to secure the ankle stabilizer 20 onto the leg B and foot C and prevent inadvertent relative shifting of stabilizer components.

The coatings 104 are also configured to restrict relative movement between the ankle stabilizer 20, the foot C, and a shoe (not shown) worn over the stabilizer 20. In particular, coating 104 applied to the aft strap face 96 of the lateral strap 28 is configured to frictionally engage an inner surface of the shoe. Furthermore, coating 104 applied to the fore strap face 94 of the medial strap 30 frictionally engages the foot C (or a sock worn on the foot C).

In use, the ankle stabilizer 20 can be applied to the ankle during the acute and/or rehabilitative stages of injury associated with the ankle joint A. Initially, the sheath 22 is slipped onto the ankle joint A by inserting the foot C into the proximal opening 34 and sliding the sheath 22 up the foot C until the foot C extends through the distal opening 36 and the heel of the foot C is received by the heel opening 38. When the ankle is received in the sheath 22, the tongue 42 stretches so that the sleeve 32 is in a stretched condition and is snugly received about the ankle. Thus, the sleeve 32 is configured to retain itself on the ankle and the sheath 22 can then be more snugly secured onto the ankle by tightening the lace 44. The secured sheath 22 provides compression of the injured tissues and ligaments surrounding the ankle joint A and is thereby configured to minimize swelling of the ankle.

The ankle stabilizer 20 is further secured by first wrapping the medial strap 30 about the ankle and securing the medial strap 30 in the secured configuration by attaching the distal strap end 92 to the medial loop fastener strip 46. The lateral strap 28 is then wrapped about the ankle and secured in the secured strap configuration by attaching the distal strap end 92 to the lateral loop fastener strip 46. As the lateral strap 28 is being wrapped and secured, the heel plate 26 is selectively positioned along the length of the strap body 84 so that the bottom of the foot C is comfortably and securely received by the heel plate 26. Furthermore, as the lateral strap 28 is wrapped and secured, the lateral strap 28 and heel plate 26 are positioned so that the heel plate 26 is located adjacent the heel of foot C, with the foot C extending rearwardly from the posterior open end 78 and forwardly from the anterior open end 76. The lateral strap 28 is tensioned so that the heel plate 26 (including base plate 60 and/or walls 62,64) is flexed into conforming engagement with sides and bottom of the foot C.

The ankle stabilizer 20 is further anchored to the leg B by wrapping and removably securing the proximal cuff 24 about the sheath 22 and the secured straps 28,30 so that the proximal cuff 24 covers and frictionally engages the attached distal strap ends 92, portions of the straps 28,30 adjacent the overlapping strap areas, the tongue 42 and the lace 44.

The ankle stabilizer 20 is removable from the ankle by first removing the proximal cuff 24. The lateral strap 28 is then removed from its secured position by detaching the respective distal strap end 92 from the lateral loop fastener strip 46 and unwinding the strap 28 from about the foot C. As a result, the heel plate 26 is also removed from the bottom of the foot C. The medial strap 30 can then be removed from its secured position by detaching the respective distal strap end 92 from the medial loop fastener strip 46. The lace 44 can then be untied to loosen the sheath 22 and allow sheath removal. In this manner, the sheath 22, heel plate 26, straps 28,30, and cuff 24 can be selectively removed from the foot C or can be re-secured, e.g., to provide the desired amount of support and comfort to the ankle.

Turning to FIGS. 11-16, an alternative ankle stabilizer 200 is depicted. For the sake of brevity, the remaining description will focus primarily on the differences of this alternative embodiment from the preferred embodiment described above. The alternative ankle stabilizer 200 is configured to provide support, stabilization, and immobilization of the ankle joint A. The stabilizer 200 is particularly configured to support the ankle joint A following a high-ankle sprain. The stabilizer 200 broadly includes a high-ankle support 202, a compressive proximal cuff 204, an alternative heel plate 206, lateral and medial stabilizing straps 208,210, and a proximal closure strip 212.

The high-ankle support 202 comprises a substantially rigid construction and is configured to be received by the leg B and ankle to stabilize and immobilize the ankle joint A. The support 202 includes a radially outer shell 214 that comprises a molded synthetic resin construction, a radially inner padding layer 216 that comprises a pliable synthetic material, such as neoprene or foam material, and lines the inside of the shell 214, and loop fastener strips 218 attached to opposite sides of shell 214 (see FIG. 12). The support 202 presents lateral and medial sides 220 that project from a closed posterior portion 221 of the support 202 (see FIG. 15). The support 202 presents proximal and distal open ends 222,224, with the sides 220 and posterior portion 221 cooperatively define an adjustable leg-receiving slot 226 that extends between the ends 222,224. The support 202 also presents opposite anterior edges 228,230 that extend between the ends 222,224 and define an anterior open face 232, with the open face 232 presenting the leg-receiving slot 226. The shell 214 and padding layer 216 are constructed to permit a limited amount of flexure between the sides 220. Furthermore, the edges 228, 230 are spaced apart to allow the sides 220 to be flexed toward and away from one another. Thus, the slot 226 can be selectively sized to receive and be compressed about the leg B and ankle.

The support 202 also presents integral proximal and distal support segments 234,236 that provide strap attachment locations (see FIGS. 12 and 15). The edges 228,230 present convex scallops 238 along the support segments 234,236 and concave scallops 240 between the support segments 234,236 spaced rearwardly from the convex scallops 238.

The medial proximal support segment 236 includes a strap connector 242 adjacent the scallop 238 and presents a slot that receives the closure strip 212, as will be discussed. The distal support segment 236 includes strap connectors 244 that each comprise an elongated rigid material strip that protrudes slightly outwardly from the corresponding side 220, are integrally formed with sides 220, and are defined by a pair of slots on either side of the strip (see FIGS. 12, 14, and 15). Furthermore, the support 202 also includes a cuff connector 246 that comprises an elongated rigid material strip that protrudes rearwardly from a rear margin 248 of the support 202 and is integrally formed with the shell 214 along the rear margin 248 (see FIGS. 15 and 16).

The closure strip 212 comprises a fabric strip with a looped end 250 and an attachment end 252 with a hook fastener strip 254. The closure strip 212 is attached to the support 202 by securing the looped end 250 to the strap connector 242 and by adjustably attaching the attachment end 252 to the lateral loop fastener strip 218. Thus, the closure strip 212 is adjustable to selectively flex the proximal support segment 234 and is thereby configured to secure the support 202 about the leg B to anchor the ankle stabilizer above the malleoli F,G.

Turning to FIGS. 11, 15, and 16, the cuff 204 is similar to cuff 24 and is attached to the cuff connector 246 of support 202. In particular, the cuff 204 is fed through slots that define the connector 246 and positioned so that lateral and medial cuff sections are presented on corresponding sides of the connector 246. The cuff sections are configured to be wrapped around the support 202, similar to the cuff 24.

Turning to FIGS. 13-16, the straps 208,210 are of identical construction compared to straps 28,30 and are attached to corresponding strap connectors 244. Specifically, a proximal end 254 of each strap 208,210 is received by and secured to the corresponding connector 244 (see FIGS. 13-15). The straps 208,210 are wrapped around the ankle in a configuration similar to the straps 28,30 of the previous embodiment. Again, the medial strap 210 is wrapped about the foot C first into the secured strap configuration (see FIG. 14). Then, the lateral strap 208 is wrapped over the medial strap 210 into the secured strap configuration (see FIGS. 11 and 14). However, compared to the attachment locations of straps 28,30, the proximal ends 254 of straps 208,210 are positioned more forwardly along the sides 220 and lower compared to the proximal open end 222.

Turning to FIGS. 13, 15, and 16, the alternative heel plate 206 comprises a unitary construction and includes an alternative base plate 256 and upright lateral and medial walls 258,260. The alternative base plate 256 includes an anterior portion that projects forwardly of the walls 258,260 to engage a large part of the sole of foot C. Consequently, the illustrated heel plate 206 is configured to provide greater support of the foot C compared to the heel plate 26.

The heel plate 206 is slidably attached to the medial strap 210, as opposed to the lateral strap 28 in the previous embodiment (see FIG. 13). Both of the straps 208,210 are wrapped around the heel plate 206 and engage an outer plate surface of the heel plate 206, particularly along the walls 258,260. In this manner, the tensioned straps 208,210 are both configured and positioned to flex the walls 258,260 inwardly toward each other so that the heel plate 206 conforms to foot C.

The ankle stabilizer 200 is applied by inserting the leg B into the slot 226 until the distal support segments 236 are in covering relationship to the malleoli F,G. Thus, the substantially rigid support 202 compresses against and restricts relative movement between the malleoli F,G. But the ankle stabilizer 200 is also configured to permit some dorsiflexion and plantar flexion of the foot C for rehabilitation purposes.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and assess the reasonably fair scope of the present invention as pertains to any apparatus not materially departing from but outside the literal scope of the invention as set forth in the following claims.

What is claimed is:

1. An ankle brace configured to provide support of the ankle joint between the leg and foot, said ankle brace comprising:
- an upper brace structure configured to be attached to the leg and anchor the ankle brace above malleoli of the joint;
- a heel plate positioned below the upper brace structure and configured to be located below the heel to anchor the ankle brace below the malleoli,
- said heel plate including a substantially flat base and upright lateral and medial walls that extend upwardly from the base; and
- an elongated strap adjustably attached to the upper brace structure and heel plate and extending exteriorly along at least one of the lateral and medial walls,
- said heel plate presenting an open longitudinal channel extending between the lateral and medial walls and operable to receive the foot,
- said heel plate having anterior and posterior open channel ends so that the channel is devoid of an upright wall, with adjustable tensioning of the strap serving to flex the at least one of the lateral and medial walls relative to the base to conform the heel plate to the heel,
- said elongated strap dimensioned and configured to extend distally from the upper brace structure to the heel plate,
- said elongated strap including a flexible fabric strip that presents opposite faces,
- said elongated strap including a high-friction coating applied to at least one of the faces and extending to the heel plate,
- said faces exhibiting a strip self-coefficient of friction and said coating exhibiting a coating self-coefficient of friction greater than the strip self-coefficient of friction, with the coating thereby configured to secure the elongated strap at the heel plate and restrict strap movement relative to the foot.

2. The ankle brace as claimed in claim 1,
said heel plate being slidably attached to the strap and selectively positionable along the length thereof.

3. The ankle brace as claimed in claim 2,
said strap presenting opposite strap ends attached to the upper brace structure,
said strap extending continuously between the strap ends and extending below at least part of the heel plate and exteriorly along the lateral and medial walls to engage and flex the heel plate securely around the foot when adjustably tensioned.

4. The ankle brace as claimed in claim 3; and
another elongated strap adjustably connecting the upper brace structure and heel plate, with the straps at least partly overlying one another adjacent the heel plate.

5. The ankle brace as claimed in claim 2,
said base presenting a slotted opening that slidably receives the strap.

6. The ankle brace as claimed in claim 1,
said coating applied to both faces and being in frictional engagement with the heel plate to further restrict strap movement relative to the heel plate.

7. The ankle brace as claimed in claim 6,
said upper brace structure comprising a flexible and tubular sheath that presents proximal and distal ends, with the proximal end being positionable on the leg and the distal end positionable on the foot,
said heel plate engaging the sheath between the ends.

8. The ankle brace as claimed in claim 7,
said coating being in frictional engagement with the sheath to further restrict strap movement relative to the sheath.

9. The ankle brace as claimed in claim 1; and
another elongated strap adjustably connecting the upper brace structure and heel plate, with the straps at least partly overlying one another adjacent the heel plate.

10. The ankle brace as claimed in claim 9,
said another elongated strap dimensioned and configured to extend distally from the upper brace structure to the heel plate,
said another elongated strap including a second flexible fabric strip that presents opposite second faces,
said another elongated strap including a second high-friction coating applied to at least one of the second faces and extending to the heel plate,
said second faces exhibiting a second strip self-coefficient of friction and said second high-friction coating exhibiting a second coating self-coefficient of friction greater than the second strip self-coefficient of friction, with the second coating thereby configured to secure the another elongated strap at the heel plate and restrict movement of the another elongated strap relative to the foot.

11. The ankle brace as claimed in claim 10,
said coatings of the respective straps being in frictional engagement with one another adjacent the heel plate to further restrict relative movement between the straps.

12. The ankle brace as claimed in claim 10,
said coatings applied to both faces of respective straps and being in frictional engagement with the heel plate to further restrict movement of the straps relative to the heel plate.

13. The ankle brace as claimed in claim 12,
said upper brace structure comprising a flexible and tubular sheath that presents proximal and distal ends, with the proximal end being positionable on the leg and the distal end positionable on the foot,
said heel plate engaging the sheath between the ends.

14. The ankle brace as claimed in claim 13,
said coatings being in frictional engagement with the sheath to further restrict strap movement relative to the sheath.

15. The ankle brace as claimed in claim 1,
said strap including first and second strap sections,
said upper brace structure presenting lateral and medial sides configured to engage the strap,
said first strap section being attached to the upper brace structure at an attachment location, with the first strap section extending horizontally from the attachment location,
said second strap section being joined to the first strap section at a downward angle spaced from the attachment location so that the second strap section is configured and dimensioned to extend between the lateral and medial sides while permitting substantially unrestricted dorsiflexion of the foot.

16. The ankle brace as claimed in claim 15,
said upper brace structure including an arcuate unitary hard shell that presents proximal and distal open ends, a closed posterior portion extending between the ends, with the lateral and medial sides projecting from the posterior portion and extending between the proximal and distal open ends,
said hard shell presenting an adjustable leg-receiving slot that extends between the open ends,
said hard shell extending continuously between the open ends to cover the malleoli and present integral proximal and distal shell segments, with the proximal shell segment dimensioned and configured to be attached above the malleoli and the distal shell segment dimensioned and configured to extend below the malleoli; and a generally horizontal adjustably tensionable closure strip attached to sides of the proximal shell segment to selectively close the slot and constrict the proximal shell segment about the leg, said elongated strap extending distally from the hard shell to the heel plate.

17. The ankle brace as claimed in claim 1, said upper brace structure comprising a flexible and tubular sheath that presents proximal and distal ends, with the proximal end being positionable on the leg and the distal end positionable on the foot, said heel plate engaging the sheath between the ends.

18. The ankle brace as claimed in claim 1, said strap including first and second strap sections, said upper brace structure presenting lateral and medial sides configured to engage the strap, said first strap section being attached to the upper brace structure at an attachment location, with the first strap section extending horizontally from the attachment location, said second strap section being joined to the first strap section at a downward angle spaced from the attachment location so that the second strap section is configured and dimensioned to extend between the lateral and medial sides while permitting substantially unrestricted dorsiflexion of the foot.

19. The ankle brace as claimed in claim 1, said upper brace structure including an arcuate unitary hard shell that presents proximal and distal open ends, a closed posterior portion extending between the ends, and lateral and medial sides projecting from the posterior portion and extending between the proximal and distal open ends, said hard shell presenting an adjustable leg-receiving slot that extends between the open ends, said hard shell extending continuously between the open ends to cover the malleoli and present integral proximal and distal shell segments, with the proximal shell segment dimensioned and configured to be attached above the malleoli and the distal shell segment dimensioned and configured to extend below the malleoli; and a generally horizontal adjustably tensionable closure strip attached to sides of the proximal shell segment to selectively close the slot and constrict the proximal shell segment about the leg, said elongated strap extending distally from the hard shell to the heel plate.

20. An ankle brace configured to provide support of the ankle joint between the leg and foot, said ankle brace comprising:

an upper brace structure configured to be attached to the leg and anchor the ankle brace above malleoli of the joint; and an elongated strap including first and second strap sections, said upper brace structure presenting lateral and medial sides configured to engage the strap, said first strap section being attached to the upper brace structure at an attachment location, with the first strap section extending horizontally from the attachment location, said second strap section being joined to the first strap section at a downward angle spaced from the attachment location so that the second strap section is configured and dimensioned to extend between the lateral and medial sides while permitting substantially unrestricted dorsiflexion of the foot, said elongated strap extending to a location below the foot and including a flexible fabric strip that presents opposite faces, said elongated strap including a high-friction coating applied to at least one of the faces and extending to the location, said faces exhibiting a strip self-coefficient of friction and said coating exhibiting a coating self-coefficient of friction greater than the strip self-coefficient of friction, with the coating thereby configured to secure the elongated strap at the lower brace structure and restrict strap movement relative to the foot.

21. The ankle brace as claimed in claim 20, said attachment location being positioned along one of the lateral and medial sides, with the second strap section being configured and dimensioned to extend to the other one of the lateral and medial sides.

22. The ankle brace as claimed in claim 21, said second strap section extending continuously from the other one of the lateral and medial sides under the foot for adjustable attachment to said one of the lateral and medial sides.

23. The ankle brace as claimed in claim 21, said first and second strap sections presenting an obtuse angle therebetween.

24. The ankle brace as claimed in claim 21;

a lower brace structure positioned below the upper brace structure and configured to be located below the heel to anchor the ankle brace below the malleoli; and another elongated strap, with the straps adjustably connecting the upper and lower brace structures and at least partly overlying one another adjacent the lower brace structure.

25. The ankle brace as claimed in claim 24, said another elongated strap including third and fourth strap segments, said third strap segment being attached to the upper brace structure at another attachment location along the other one of the lateral and medial sides, with the third strap section extending horizontally from the another attachment location, said fourth strap section being joined to the third strap section at another downward angle spaced from the another attachment location so that the fourth strap section is configured and dimensioned to extend to the one of the lateral and medial sides to permit substantially unrestricted dorsiflexion of the foot.

26. The ankle brace as claimed in claim 20, said upper brace structure comprising a flexible and tubular sheath that presents proximal and distal ends, with the proximal end being positionable on the leg and the distal end positionable on the foot, said strap being attached to the sheath between the ends.

27. The ankle brace as claimed in claim 20; and a lower brace structure positioned below the upper brace structure and configured to be located below the heel to anchor the ankle brace below the malleoli, said lower brace structure comprising a heel plate that includes a substantially flat base and upright lateral and medial walls that extend upwardly from the base.

28. The ankle brace as claimed in claim 27, said first and second strap sections presenting a pair of opposite strap ends, said opposite strap ends attached to the upper brace structure, said strap extending continuously between the strap ends and extending below the heel plate to engage and flex the lateral and medial walls toward one another.

29. The ankle brace as claimed in claim 20, said upper brace structure including an arcuate unitary hard shell that presents proximal and distal open ends, a closed posterior portion extending between the ends, and lateral and medial sides projecting from the posterior portion and extending between the proximal and distal open ends, said hard shell presenting an adjustable leg-receiving slot that extends between the open ends, said hard shell extending continuously between the open ends to cover the malleoli and present integral proximal and distal shell segments, with the proximal shell segment dimensioned and configured to be attached above the malleoli and the distal shell segment dimensioned and configured to extend below the malleoli; and a generally horizontal adjustably tensionable closure strip attached to sides of the proximal shell segment to selectively close the slot and constrict the proximal shell segment about the leg, said elongated strap extending distally from the hard shell to a location below the foot.

30. An ankle brace configured to provide support of the ankle joint between the leg and foot, said ankle brace comprising:

an upper brace structure configured to be attached to the leg and anchor the ankle brace above malleoli of the joint; and an elongated strap adjustably attached to the upper brace structure, said elongated strap dimensioned and configured to extend distally from the upper brace structure to a location below the foot, said elongated strap including a flexible fabric strip that presents opposite faces, said elongated strap including a high-friction coating applied to at least one of the faces and extending to the location, said faces exhibiting a strip self-coefficient of friction and said coating exhibiting a coating self-coefficient of friction greater than the strip self-coefficient of friction, with the coating thereby configured to secure the elongated strap at the location and restrict strap movement relative to the foot.

31. The ankle brace as claimed in claim 30, said coating including a material selected from the group consisting of latex, natural rubber, synthetic rubber, and neoprene.

32. The ankle brace as claimed in claim 30, said coating self-coefficient of friction being greater than about 0.2.

33. The ankle brace as claimed in claim 30; and a lower brace structure positioned below the upper brace structure, said lower brace structure presenting an anchoring location and being positionable below the heel to anchor the ankle brace below the malleoli, said anchoring location corresponding with the location to which the strap extends.

34. The ankle brace as claimed in claim 33, said coating applied to both faces and being in frictional engagement with the lower brace structure to further restrict strap movement relative to the lower brace structure.

35. The ankle brace as claimed in claim 34, said upper brace structure comprising a flexible and tubular sheath that presents proximal and distal ends, with the proximal end being positionable on the leg and the distal end positionable on the foot, said strap being attached to the sheath between the ends.

36. The ankle brace as claimed in claim 35, said coating being in frictional engagement with the sheath to further restrict strap movement relative to the sheath.

37. The ankle brace as claimed in claim 33; and another elongated strap adjustably connecting the upper and lower brace structures, with the straps at least partly overlying one another adjacent the lower brace structure.

38. The ankle brace as claimed in claim 37, said another elongated strap dimensioned and configured to extend distally from the upper brace structure to the lower brace structure, said another elongated strap including a second flexible fabric strip that presents opposite second faces, said another elongated strap including a second high-friction coating applied to at least one of the second faces and extending to the lower brace structure, said second faces exhibiting a second strip self-coefficient of friction and said second high-friction coating exhibiting a second coating self-coefficient of friction greater than the second strip self-coefficient of friction, with the second coating thereby configured to secure the another elongated strap at the lower brace structure and restrict movement of the another elongated strap relative to the foot.

39. The ankle brace as claimed in claim 38, said coatings of the respective straps being in frictional engagement with one another adjacent the lower brace structure to further restrict relative movement between the straps.

40. The ankle brace as claimed in claim 38, said coatings applied to both faces of respective straps and being in frictional engagement with the lower brace structure to further restrict movement of the straps relative to the lower brace structure.

41. The ankle brace as claimed in claim 40, said upper brace structure comprising a flexible and tubular sheath that presents proximal and distal ends, with the proximal end being positionable on the leg and the distal end positionable on the foot, said heel plate engaging the sheath between the ends.

42. The ankle brace as claimed in claim 41, said coatings being in frictional engagement with the sheath to further restrict strap movement relative to the sheath.

43. The ankle brace as claimed in claim 33, said lower brace structure comprising a heel plate that includes a substantially flat base and upright lateral and medial walls that extend upwardly from the base.

44. The ankle brace as claimed in claim 33, said upper brace structure comprising a flexible and tubular sheath that presents proximal and distal ends, with the proximal end being positionable on the leg and the distal end positionable on the foot, said heel plate engaging the sheath between the ends.

* * * * *